US012582801B2

(12) United States Patent
Ando et al.

(10) Patent No.: US 12,582,801 B2
(45) Date of Patent: Mar. 24, 2026

(54) MEDICAL DEVICE

(71) Applicant: TOGO MEDIKIT CO., LTD., Tokyo (JP)

(72) Inventors: Hirokazu Ando, Tokyo (JP); Takahiro Shibata, Tokyo (JP)

(73) Assignee: TOGO MEDIKIT CO., LTD., Bunkyo-ku (JP)

( * ) Notice: Subject to any disclaimer, the term of this patent is extended or adjusted under 35 U.S.C. 154(b) by 302 days.

(21) Appl. No.: 18/247,813

(22) PCT Filed: Oct. 21, 2021

(86) PCT No.: PCT/JP2021/038927
§ 371 (c)(1),
(2) Date: Apr. 4, 2023

(87) PCT Pub. No.: WO2022/085761
PCT Pub. Date: Apr. 28, 2022

(65) Prior Publication Data
US 2023/0372672 A1 Nov. 23, 2023

(30) Foreign Application Priority Data
Oct. 22, 2020 (JP) ................................. 2020-177200

(51) Int. Cl.
*A61M 25/01* (2006.01)
(52) U.S. Cl.
CPC ............................... *A61M 25/0113* (2013.01)
(58) Field of Classification Search
CPC .......... A61M 25/0113; A61M 25/0136; A61M 25/0147; A61M 2025/015
See application file for complete search history.

(56) References Cited

U.S. PATENT DOCUMENTS 7,691,095 B2 * 4/2010 Bednarek .......... A61M 25/0147
604/524
2003/0120259 A1 * 6/2003 Mickley ............ A61M 25/0147
604/528
(Continued)

FOREIGN PATENT DOCUMENTS

JP 2006-187606 A 7/2006
JP 2011-055848 A 3/2011
(Continued)

OTHER PUBLICATIONS

International Search Report from PCT/JP2021/038927 Dec. 7, 2021, 4 pgs.
(Continued)

*Primary Examiner* — Diane D Yabut
*Assistant Examiner* — Christian D Knauss
(74) *Attorney, Agent, or Firm* — Tutunjian & Bitetto, P.C.

(57) ABSTRACT

A medical device that can prevent the rotating operation part from rotating more than the operator's intention and improve the operability to control the direction of the head of the tubular member is provided. The medical device includes a flexible tubular member and a rotating operation part that deflects the head of the tubular member in a first direction when rotating in positive rotation direction and deflects the head of the tubular member in a second direction when rotating in negative rotation direction opposite to the positive direction. A handle case is gripped when the rotating operation part is rotated. An O-ring that is placed between the rotating operation part and the handle case produces frictional force between the rotating operation part and the handle case when the rotating operation part is rotated.

15 Claims, 28 Drawing Sheets

(56)  References Cited

U.S. PATENT DOCUMENTS

| 2014/0018732 A1* | 1/2014 | Bagaoisan | ........ A61M 25/0136 |
| | | | 604/95.04 |
| 2016/0058975 A1* | 3/2016 | Kimmel | ............ A61M 25/0147 |
| | | | 600/411 |
| 2016/0206853 A1* | 7/2016 | Bolduc | ............. A61M 25/0136 |

FOREIGN PATENT DOCUMENTS

| JP | 2016-511375 A | 4/2016 |
| JP | 2016-171893 A | 9/2016 |
| JP | 2018-099480 A | 6/2018 |
| JP | 2020-501836 A | 1/2020 |
| JP | 2020-62181 A | 4/2020 |

OTHER PUBLICATIONS

Japanese 1st Office Action JP2020-177200, Issued Feb. 2, 2021, 6 pgs.
Japanese 2nd Office Action JP2020-177200, Issued Jun. 8, 2021, 6 pgs.

* cited by examiner

Two projections facing each other

Four projections

All around projection

MEDICAL DEVICE

TECHNICAL FIELD

The present disclosure relates to a medical device. Specifically, the present disclosure relates to a medical device provided with a flexible tubular member for medical use, such as a tube for sheath, catheter, or endoscope, which can control the direction of the head of the tubular member.

BACKGROUND ART

Conventionally, this type of the medical device is, for example, disclosed in Patent Documents 1 and 2. The medical device (interactively promotable catheter control handle) disclosed in Patent Document 1 is a handle for controlling the flexure of the end of the main body of a catheter containing the first and the second flexible wires, which includes:

a slide base including a first edge, a second edge, and a slide chamber extending in a longer direction in at least a part of the slide base;

an adjustment knob being rotatably connected with the first edge of the slide base, in which a hole extends, at least a part of the internal diameter of the hole including an inside right screw and an inside left screw;

a first slide being placed in the slide chamber, being connected to the first flexible wire, the first slide including an outside right screw; and a second slide being placed in the slide chamber, being connected to the second flexible wire, the second slide including an outside left screw, in which the inside screws of the adjustment knob are engaged with the outside screws of the slide, and the slides are displaced in mutually opposite direction in the slide chamber by rotating the adjustment knob (refer to claim 1 described in Patent Document 1).

The medical device disclosed in Patent Document 2 includes:

a housing into which the base end of a tube with a head flexible part is inserted;

a rotating operation part being rotatably placed around the axis in the longitudinal direction of the housing;

a rotating shaft being placed in the housing, the rotating shaft rotating in the operating direction of the rotating operation part, in which a right screw and a left screw are formed in the same region of the outer periphery, the leads of the screws being equal to each other;

a first slider having a gutter-shaped part in which a screw being threadably mountable on one of the right screw or the left screw of the rotating shaft is formed in the inner periphery, the first slider moving from the home position toward the base end along the rotating shaft by rotating the rotating operation part clockwise when the head flexible part of the tube is linear shaped, the first slider moving from the home position toward the head end along the rotating shaft by rotating the rotating operation part counter-clockwise when the head flexible part of the tube is linear shaped;

a second slider having gutter-shaped part in which a screw being placed threadably mountable on the other of the right screw or the left screw of the rotating shaft is formed in the inner periphery, the second slider moving from the home position a distance equal to the moving distance of the first slider toward the head end along the rotating shaft by rotating the rotating operation part clockwise when the head flexible part of the tube is linear shaped, the second slider moving a distance equal to the moving distance of the first slider from the home position toward the base end along the rotating shaft by rotating the rotating operation part counter-clockwise when the head flexible part of the tube is linear shaped;

a first anchor being placed connectably with/disconnectably from the first slider in the base end side of the first slider, in which the base end of a first operation wire for deflecting the head of the tube in a first direction is fixed, the first anchor being movably from the neutral position located when the head flexible part of the tube is shaped linear to the head- or base-end direction, the first anchor moving in the base-end direction along the rotating shaft with making contact with the first slider when the first slider moves to the base-end direction;

a second anchor being placed connectably with/disconnectably from the second slider in the base end side of the second slider, in which the base end of the second operation wire for deflecting the head of the tube in a second direction is fixed, the second anchor being movably from the neutral position located when the head flexible part of the tube is shaped linear to the head- or base-end direction, the second anchor moving in the base-end direction along the rotating shaft with making contact with the second slider when the second slider moves to the base-end direction; and a medical tube having a head flexible part, the base end of which is inserted in the housing of the handle (Refer to claims 1 and 6 described in Patent Document 2).

In the medical devices disclosed in Patent Documents 1 and 2, the two semicircular column-shaped sliders (slides) slide in mutually opposite direction (Refer to paragraph 0029, FIGS. 2 and 4, and reference numerals 30 and 32 of Patent Document 1, and FIG. 2, and reference numerals 41 and 42 of Patent Document 2) to cause uneasy rotating operation of the rotating operation part (dial) due to the friction generated between the two sliders (slides). This leads to hardly control the flexure (direction of the head) at the end of the main body of the catheter (tubular member).

The medical device that can improve the operability to control the direction of the head of the tubular member by minimizing torque transmitting to the rotating operation part (dial) is proposed (Patent Document 3). In the medical device proposed in Patent Document 3, a first moving material (first slide) and a second moving member (second slide) are placed away from each other.

DOCUMENT IN THE EXISTING ART

Patent Document

Patent Document 1: JP 4468296 B
Patent Document 2: JP 6693861 B
Patent Document 3: JP 2020-062181 A

SUMMARY

The Technical Problem Solved by the Disclosure

According to the medical device proposed in Patent Document 3, the rotating operation of the rotating operation part (dial) is easy, and the transmission efficiency of the rotary driving force from the main gear to the first and the second gears is excellent. However, the rotating operation part, (dial) may rotate more than the operator's intent. This makes the fine adjustment difficult when the flexure of the end (the direction of the head) of the main body of the catheter (tubular member). From this viewpoint, the medical device remains to be improved.

An objective of the present disclosure is to provide a medical device that can prevent the rotating operation part (dial) from rotating more than the operator's intent and improve the operability to control the direction of the head of the tubular member.

Solution for Solving the Technical Problem

According to the first aspect of the present disclosure, a medical device includes:

a flexible tubular member;

a rotating operation part that deflects the head of the tubular member in a first direction when rotating in positive rotation direction and deflects the head of the tubular member in a second direction when rotating in negative rotation direction opposite to the positive rotation direction;

a gripper that is gripped when the rotating operation part is operated to rotate; and a friction member that is placed between the rotating operation part and the gripper and produces frictional force in the direction opposite to the rotation direction of the rotating operation part between the rotating operation part and the gripper when the rotating operation part is operated to rotate, in which a projection that is in contact with the friction member and adjusts the frictional force in the direction opposite to the rotation direction of the rotating operation part is placed on the inner face of the gripper.

The medical device according to the first aspect of the present disclosure has the following function effect. Since the friction member is placed between the rotating operation part (dial) and the gripper (handle case) and produces frictional force in the direction opposite to the rotation direction of the rotating operation part between the rotating operation part and the gripper when the rotating operation part is operated to rotate, an appropriate load is applied to the operation of the handle (rotating operation part (dial)+ gripper (handle case)) to rotate the rotating operation part at an appropriate load not too heavily or lightly. Since the projection that is in contact with the friction member and adjusts the frictional force in the direction opposite to the rotation direction of the rotating operation part is placed on the inner face of the gripper, a constant brake can be applied to the rotation of the rotating operation part (dial) by adjusting the frictional force between the rotating operation part (dial) and the gripper (handle case). Accordingly, the medical device according to the first aspect of the present disclosure can prevent the rotating operation part (dial) from rotating more than the operator's intent and improve the operability to control the direction of the head of the tubular member.

The medical device according to the first aspect of the present disclosure preferably has the below-mentioned configuration according to any one of the second to ninth aspects of the present disclosure. According to the second aspect of the present disclosure, the medical device according to the first aspect of the present disclosure further includes a second friction member that is placed between the rotating operation part and the tubular member and produces frictional force in the direction opposite to the rotation direction of the rotating operation part between the rotating operation part and the tubular member when the rotating operation part is operated to rotate. According to the second aspect of the present disclosure, since a second friction member is placed between the rotating operation part and the tubular member and produces frictional force in the direction opposite to the rotation direction of the rotating operation part between the rotating operation part and the tubular member when the rotating operation part is operated to rotate, a more appropriate load is applied to the operation of the handle (rotating operation part (dial)+gripper (handle case)) to rotate the rotating operation part at a more appropriate load not too heavily or lightly.

According to the third aspect of the present disclosure, the medical device according to the first or the second aspect of the present disclosure further includes:

a first feed rod where the first moving member moves;

a second feed rod where the second moving member moves;

a first operation wire that has a first end fixed to the head of the tube member and a second end fixed to the first moving member or the first other member working with the first moving member;

a second operation wire that has a first end fixed to the head of the tube member and a second end fixed to the second moving member or the second other member working with the second moving member;

a first gear fixed to the first feed rod;

a second gear fixed to the second feed rod; and a main gear that is placed between the first gear and the second gear and rotates by rotating the rotating operation part to transmit rotary driving force to the first gear and the second gear, in which the first moving member is moved to the base end side when the rotating operation part is rotated in the positive rotation direction to allow the first operation wire to deflect the head of the tubular member in the first direction, and the second moving member is moved to the base end side when the rotating operation part is rotated in the negative rotation direction to allow the second operation wire to deflect the head of the tubular member in the second direction.

According to the third aspect of the present disclosure, since the first moving member (first slide) and the second moving member (second slide) are placed away from each other, no transmission power is lost by friction generated between the two moving members (slides). Therefore, since no strong torque transmitting to the rotating operation part (dial) is necessary, the operability when the direction of the head of the tubular member is controlled can be greatly improved.

According to the fourth aspect of the present disclosure, in the medical device according to any one of the first to the third aspect of the present disclosure, the rotating operation part is located in the head side of the gripper (positive handle). According to the fifth aspect of the present disclosure, in the medical device according to the fourth aspect of the present disclosure, the tubular member is fixed in the base end side of the gripper. According to the fifth aspect of the present disclosure, since the tubular member is fixed in the base end side of the gripper (handle case), the tubular member is prevented from twisting in the gripper (handle case) by, for example, placing the friction member in the space shared with the tubular member in the rotating operation part (dial) located in the head side of the gripper (handle case) so that the torque produced by the rotating operation of the gripper (handle case) can be easily transmitted to the tubular member. Therefore, the tubular member is prevented from twisting by completely matching the rotation of the gripper (handle case) with that of the tubular member so that the rotation of the gripper (handle case) can be directly transmitted to the tubular member. Moreover, the pushability to certainly transmit pushing force from the operator to the head of the tubular member can be improved. Therefore, when the gripper (handle case) is pushed straight, the tubular member is also pushed straight.

According to the sixth aspect of the present disclosure, in the medical device according to any one of the first to the third aspects of the present disclosure, the rotating operation part is located in the base side of the gripper (negative handle).

According to the seventh aspect of the present disclosure, in the medical device according to the sixth aspect of the present disclosure, the head of the tubular member is fixed in the head end side of the gripper. According to the seventh aspect of the present disclosure, since the tubular member is fixed in the head end side of the gripper (handle case), the torque produced by the rotating operation of the gripper (handle case) can be easily transmitted to the tubular member. Therefore, the tubular member is prevented from twisting by completely matching the rotation of the gripper (handle case) with that of the tubular member so that the rotation of the gripper (handle case) can be directly transmitted to the tubular member. Moreover, the pushability to certainly transmit pushing force from the operator to the head of the tubular member can be improved. Therefore, when the gripper (handle case) is pushed straight, the tubular member is also pushed straight.

According to the eighth aspect of the present disclosure, in the medical device according to any one of the first to the seventh aspects of the present disclosure, the gripper includes a first gripper member and a second gripper member that are approximately semicircular column-shaped and placed opposite to each other, and the first gripper member and the second gripper member are detachably integrated with each other. According to the eighth aspect of the present disclosure, the medical device can be easily disassembled. Therefore, the handle (rotating operation part (dial)+gripper (handle case)) is easily recycled, and the medical device using this handle can be reproduced.

According to the ninth aspect of the present disclosure, in the medical device according to any one of the first to the eighth aspects of the present disclosure, a display indicating the turning angle of the head of the tubular member along the circumferential direction is provided in a part of the rotating operation part that is inserted in the gripper, and a window through which the display can be seen from outside is provided in the gripper. According to the ninth aspect of the present disclosure, the turning angle of the head of the tubular member can be accurately controlled by operating the rotating operation part (dial) to rotate while "the display indicating the turning angle of the head of the tubular member" is being watched.

Technical Effect

According to the present disclosure, an appropriate load can be applied to the operation of the handle (rotating operation part (dial)+gripper (handle case)) to rotate the rotating operation part at an appropriate load not too heavily or lightly. Therefore, the present disclosure can prevent the rotating operation part (dial) from rotating more than the operator's intent and improve the operability to control the direction of the head of the tubular member.

BRIEF DESCRIPTION OF THE DRAWINGS

(FIG. 9A is a plan view illustrating the situation in which only the rotating operation part (dial) is assembled in the gripper (handle case), FIG. 9B is a partially enlarged view illustrating the situation in which the O-ring is put as a friction member, and FIG. 9C is a partially enlarged view illustrating the situation in which the O-ring is not put as a friction member.)

(FIG. 11A is a side view around the rotating operation part (dial), FIG. 11B is a cross-sectional view of FIG. 11A along the line D-D, FIG. 11C is a cross-sectional view illustrating another aspect of the projections.)

(FIG. 12A is a perspective view illustrating the first case member, FIG. 12B is a side view illustrating the situation in which the gripper (handle case) is disassembled, and FIG. 12C is a side cross-sectional view illustrating how to assemble and disassemble the gripper (handle case).)

(FIG. 15A is a side view illustrating the gripper (handle case), and FIGS. 15B to 15D are diagrams of the gripper (handle case) viewed from the direction of the arrow P in FIG. 15A.)

DETAILED DESCRIPTION OF THE EMBODIMENTS

The present disclosure will be more specifically described below with reference to the preferable Embodiments. However, these are illustrative only, and the present disclosure is not limited thereto.

Embodiment 1

Configuration of Medical Device

The configuration of the medical device 1 according to Embodiment 1 of the present disclosure is described below with reference to FIGS. 1 to 12C, giving an example where the tubular member is an introducer sheath.

Figure 1:
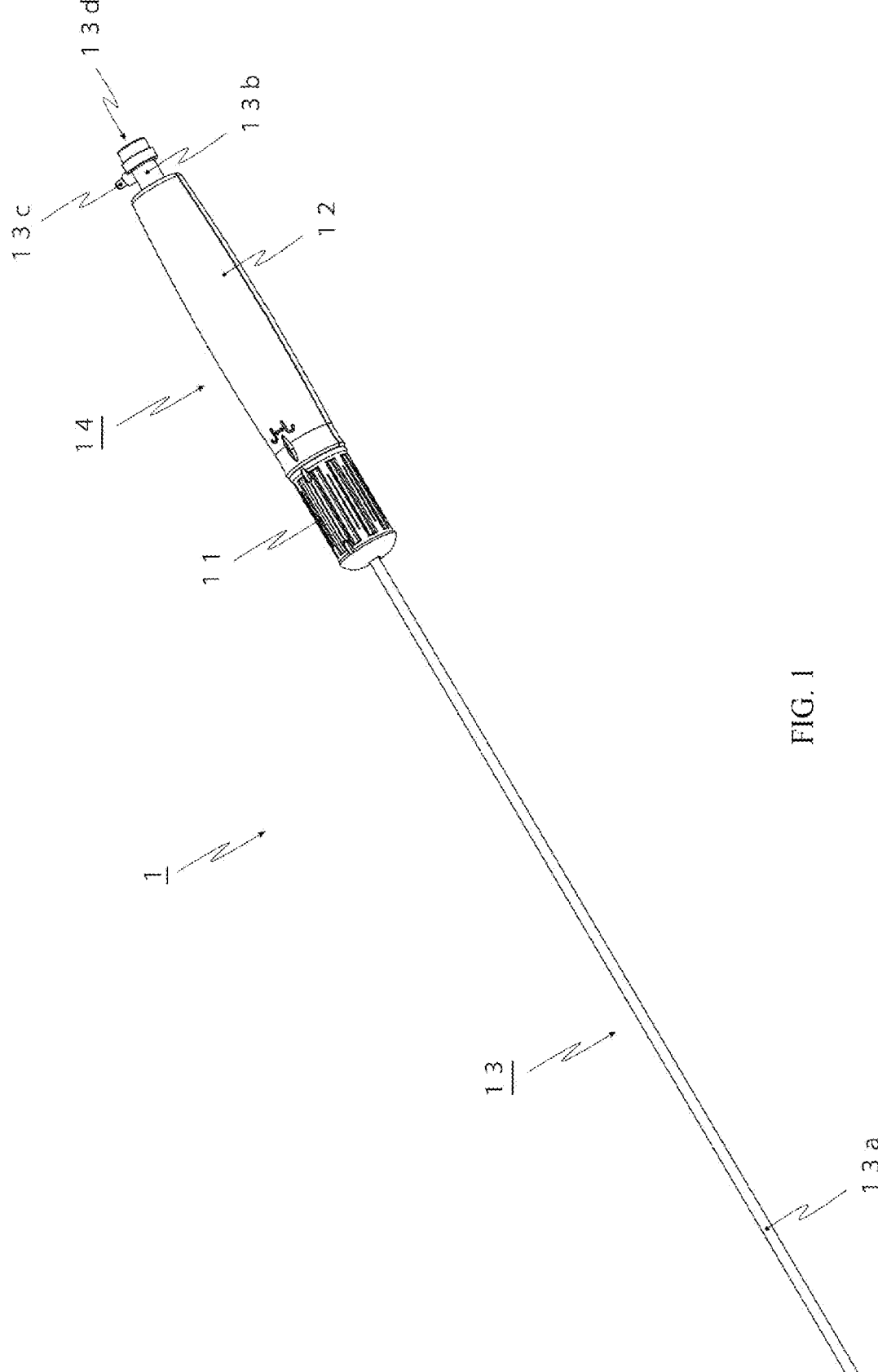
FIG. 1 is a perspective view illustrating the configuration of the medical device according to Embodiment 1 of the present disclosure.
Figure 2:
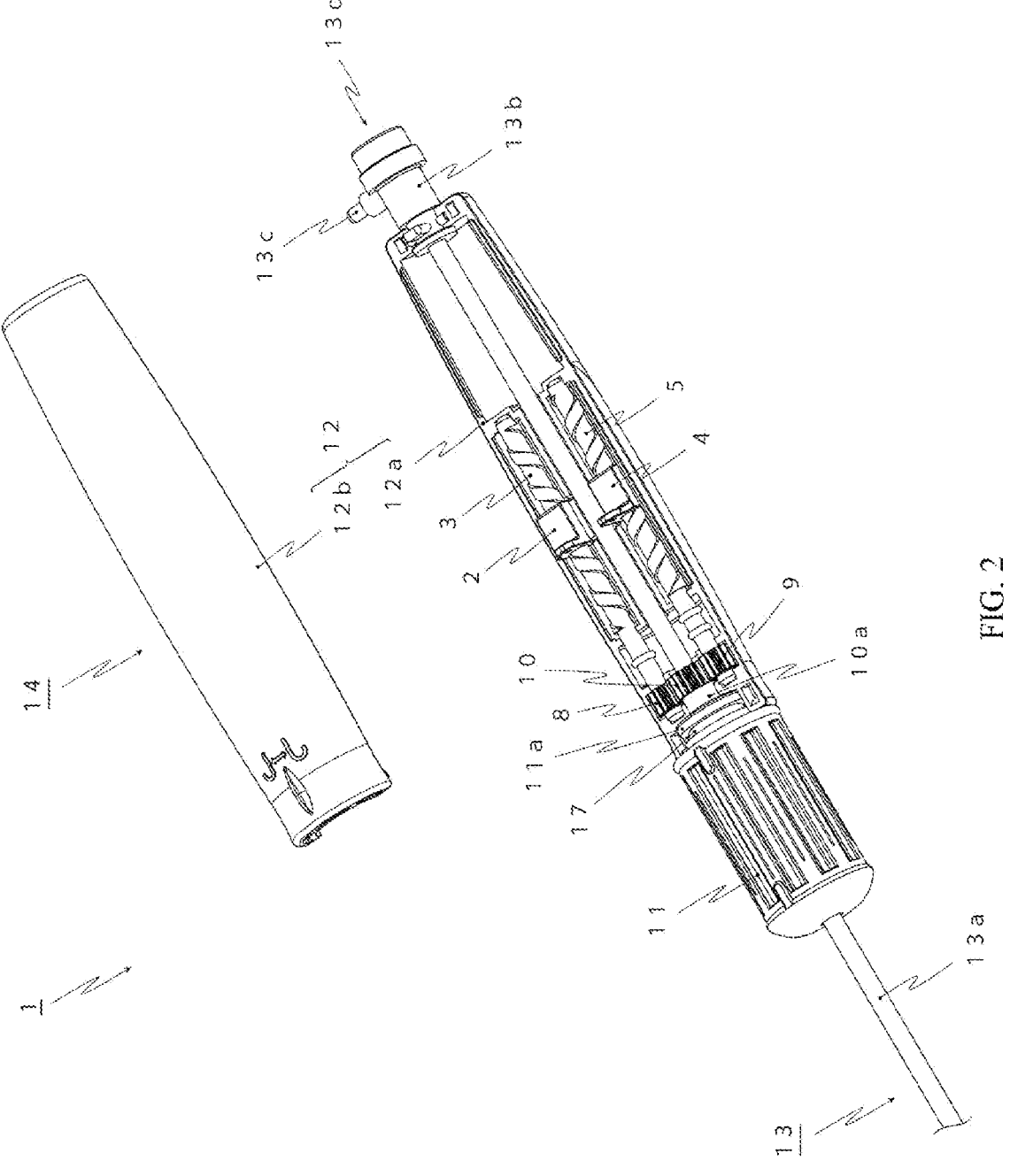
FIG. 2 is a perspective view illustrating an internal mechanism of the medical device according to Embodiment 1 of the present disclosure. (The second case member is detached, and the first and the second operation wires are omitted.)
Figure 3:
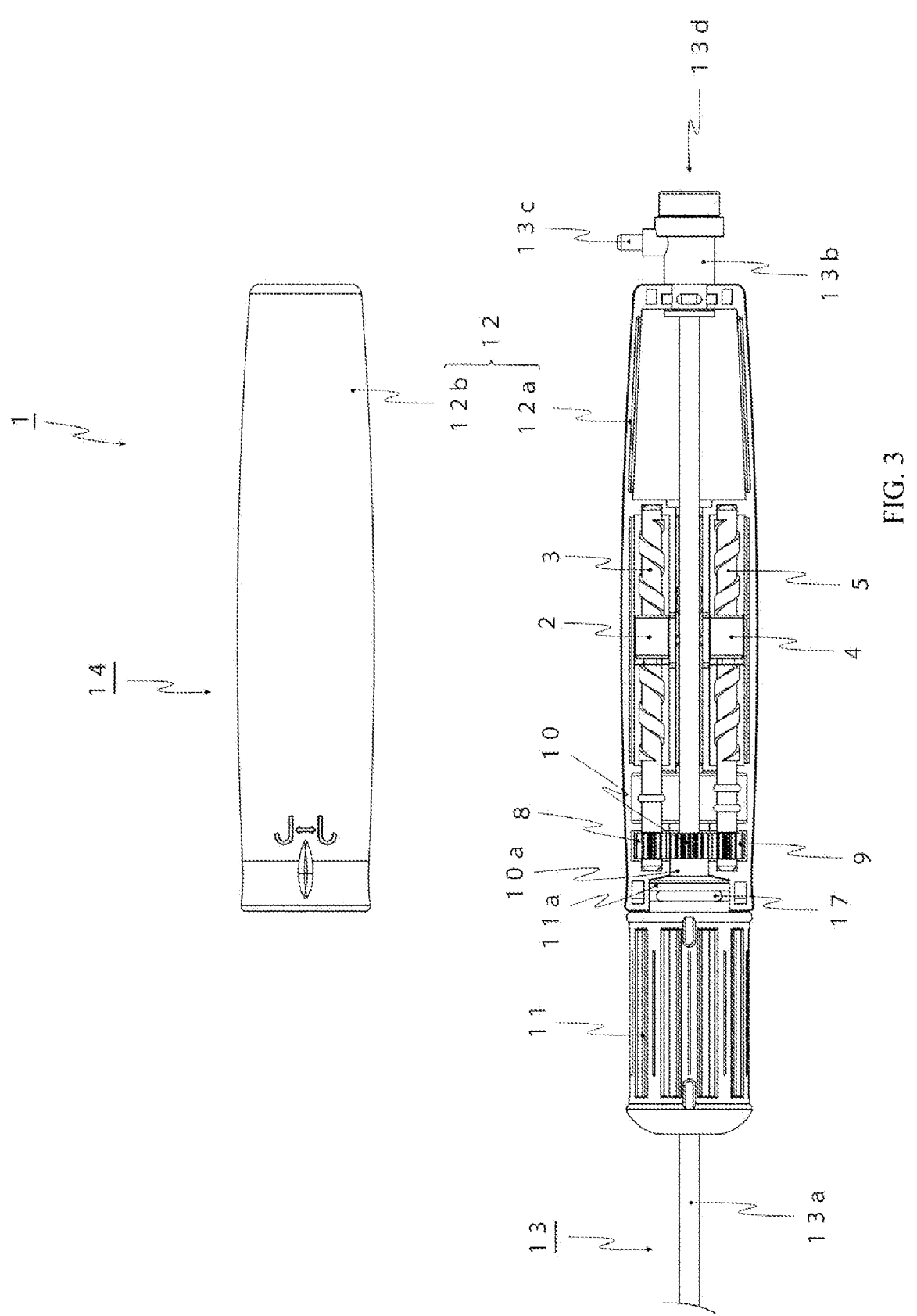
FIG. 3 is a plan view illustrating an internal mechanism of the medical device according to Embodiment 1 of the present disclosure. (The second case member is detached, and the first and the second operation wires are omitted.)

The medical device 1 shown in FIG. 1 is a head deflectable sheath provided with an introducer sheath 13 and a handle 14. The sheath 13 is formed of a flexible tubular member. The handle 14 controls the direction of the head of the sheath 13. The introducer sheath 13 is provided with a sheath tube 13a and a sheath hub 13b, a side port 13c, and a hemostasis valve (not shown) built in the sheath hub 13b. The sheath hub 13b is placed at the base end of the sheath tube 13a. The side port 13c is integrally formed with the sheath hub 13b and communicated with the inside of the sheath tube 13a. The hemostasis valve is double layered so that hemostatic effect can be expected compared with a single-layered valve. The sheath 13 is used integrally with a dilator (not shown) when a cardiac catheter is inserted into the atria and ventricles from a blood vessel, for example. The dilator insertion opening 13d to insert a dilator is placed at the back end of the sheath hub 13b.

A three-way cock (not shown) is attached to the side port 13c through a side tube (not shown). To prevent air from being mixed into a blood vessel, heparin saline is injected from the three-way cock into the sheath tube 13a before the sheath tube 13a is inserted into a blood vessel. (The air is substituted with saline.) Moreover, the three-way cock is used to suck out the mixed air when the dilator is pulled out or when another device used in combination is inserted into or pulled out from the sheath tube 13a after the sheath tube 13a is inserted in a blood vessel. In addition, medical solution is injected from the three-way cock.

The material of the sheath tube 13a is preferably a biocompatible synthetic resin selected from polyether block amide, polyamide (nylon 11), and polytetrafluoroethylene, for example. The material of the sheath hub 13b is preferably a hard material such as a hard resin. The example of the hard resin includes polyethylene, polypropylene, polyamide, polycarbonate, and polystyrene. The example of the material of the hemostasis valve includes an ABS resin and a silicone rubber.

As shown in FIGS. 1 to 3, 6, and 7, the handle 14 is provided with a rotating operation part (dial) 11 at the head end and an approximately column-shaped handle case 12 (gripper) at the back end (positive handle). The rotating operation part (dial) 11 is formed in an approximate column-shape, the diameter of which is approximately equal to that of the handle case 12, which rotates the main gear 10 described later. The handle case 12 is formed by mutually assembling an approximately semicircular column-shaped first case member (first gripper member) 12a and an approximately semicircular column-shaped second case member (second gripper member) 12b that are placed opposite to each other. The handle case 12 accommodates a first moving member 2, a first feed rod 3, a second moving member 4, a second feed rod 5, a first gear 8, a second gear 9, and a main gear 10. The first moving member 2 is formed in an approximate cuboid-shape, which moves on the first feed rod 3 in the longitudinal direction. The second moving member 4 is formed in an approximate cuboid-shape, which moves on the second feed rod 5 in the longitudinal direction. The first feed rod 3 and the second feed rod 5 are arranged at intervals of approximate 180 degrees in circumferential direction and accommodated away from each other. The first gear 8 is fixed at the head end of the first feed rod 3. The second gear 9 is fixed at the head end of the second feed rod 5. The main gear 10 is placed between the first gear 8 and the second gear 9, which transmits rotary driving force in the same direction as those of the first gear 8 and the second gear 9.

Figure 4:
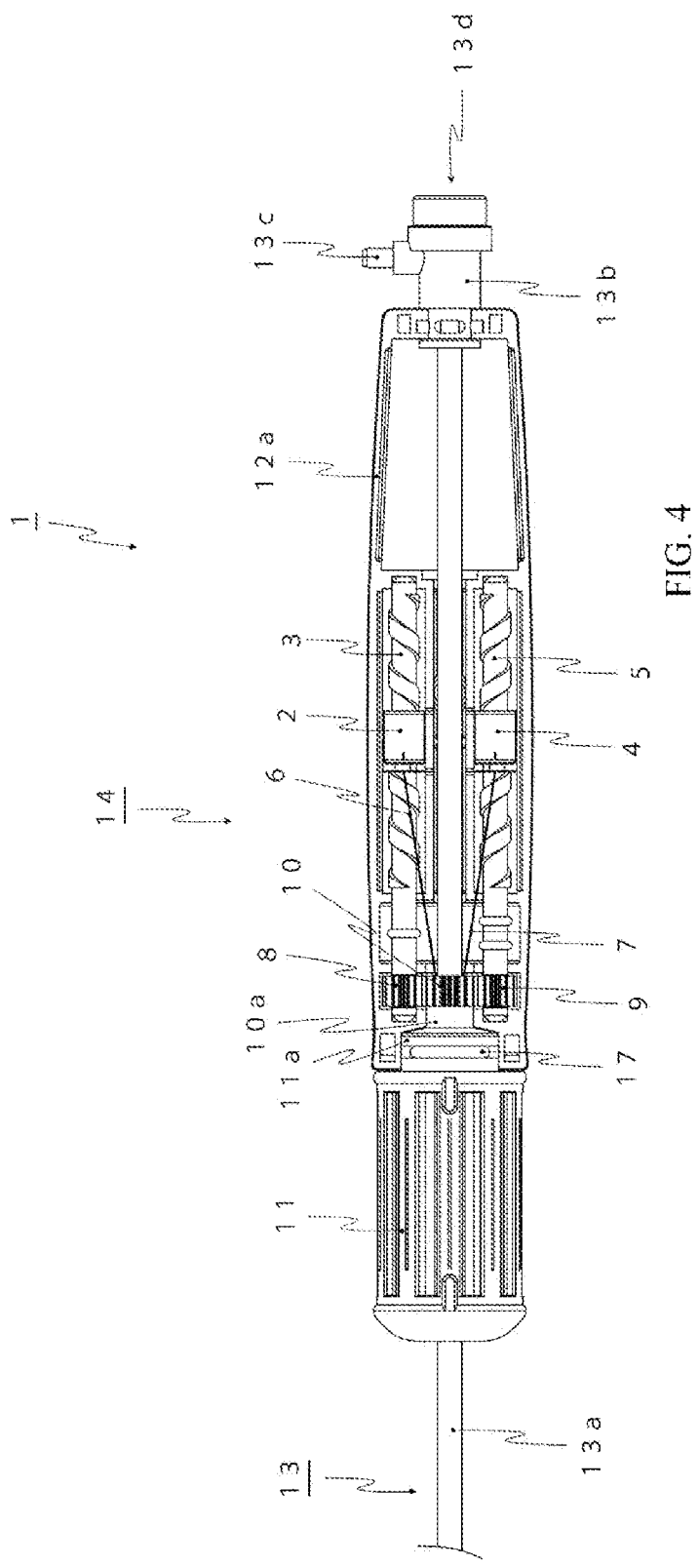
FIG. 4 is a plan view illustrating an internal mechanism of the medical device according to Embodiment 1 of the present disclosure. (The second case member is omitted.)
Figure 5:
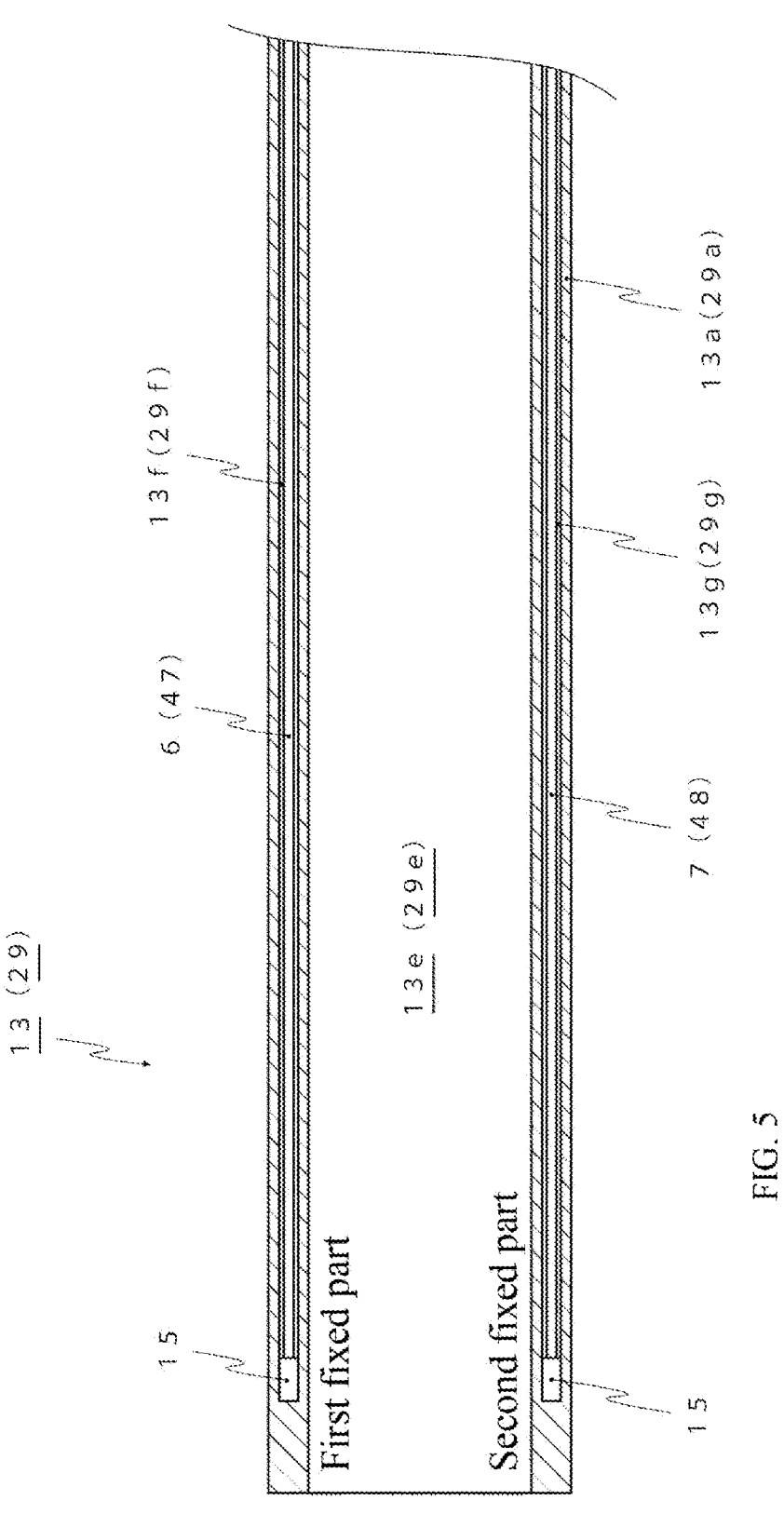
FIG. 5 is a top sectional view illustrating the configuration of the head of the tubular member part that is one of the components of the medical device according to Embodiments 1 and 3 of the present disclosure.

As shown in FIGS. 4 and 5, the first end of the first operation wire 6 is fixed at the head of the sheath tube 13a, and the second end of the first operation wire 6 is fixed at the first moving member 2. The first end of the second operation wire 7 is fixed at the head of the sheath tube 13a, and the second end of the second operation wire 7 is fixed at the second moving member 4. The first fixed part at which the first end of the first operation wire 6 is fixed and the second fixed part at which the first end of the second operation wire 7 is fixed are placed opposite to each other.

Figures 13A, 13B:
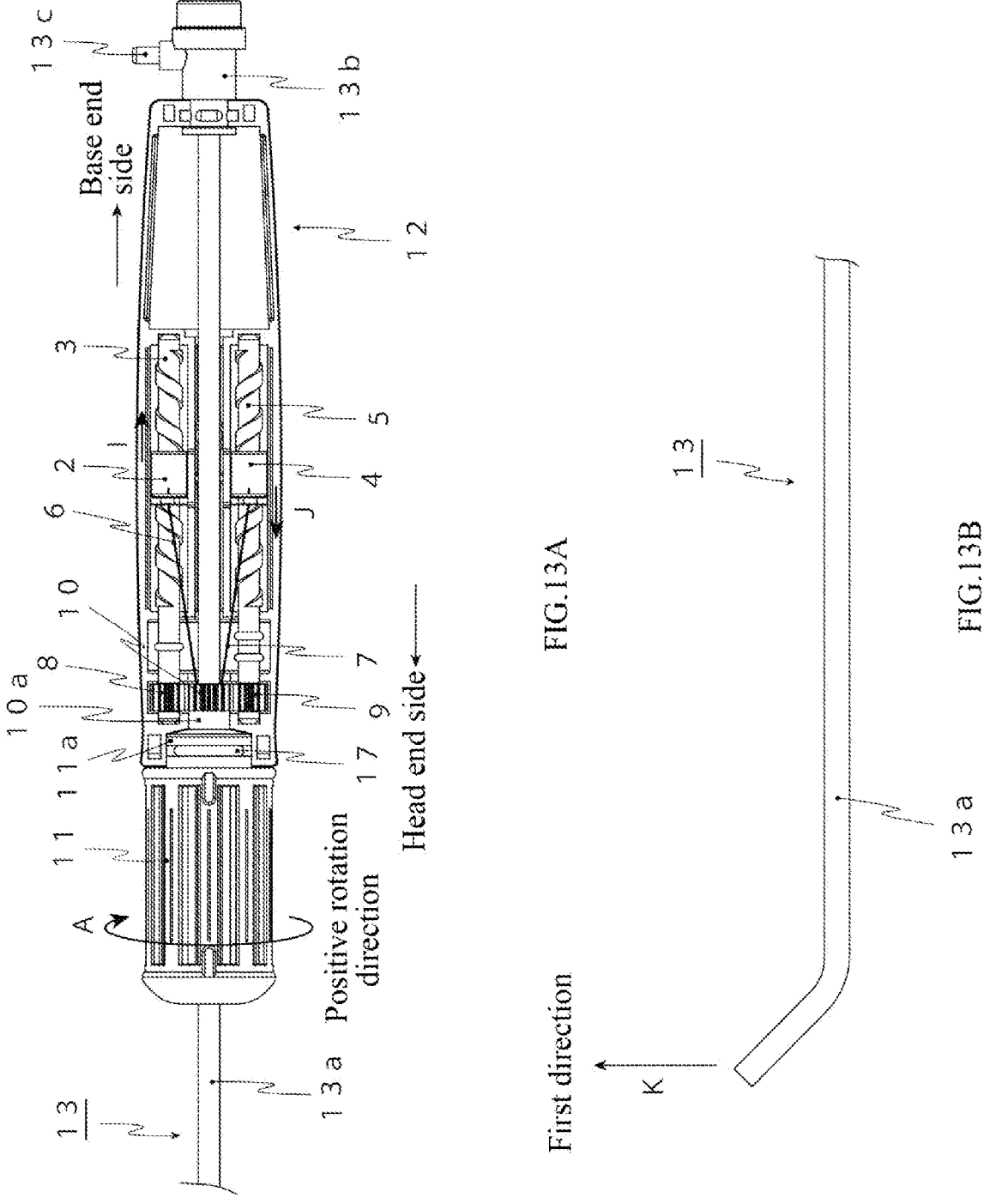
FIGS. 13A-13B are a plan view illustrating the first example use of the medical device according to Embodiment 1 of the present disclosure.

The first moving member 2 is moved to the base end side when the rotating operation part 11 is rotated in the positive rotation direction to allow the first operation wire 6 to deflect the head of the sheath tube 13a in a first direction (refer to FIGS. 13A-13B). The second moving member 4 is moved to the base end side when the rotating operation part 11 is rotated in the negative rotation direction opposite to the positive rotation direction to allow the second operation wire 7 to deflect the head of the sheath tube 13a in a second direction opposite to the first direction (refer to FIGS. 14A-14B). The number of the teeth of the first gear 8 and the number of the teeth of the second gear 9 are the same. The pitch of the male thread of the first feed rod 3 and the pitch of the male thread of the second feed rod 5 are also the same. Accordingly, the curve shape of the head of the sheath tube 13a when the rotating operation part 11 is rotated in the positive rotation direction is approximately the same as that when the rotating operation part 11 is rotated in the negative rotation direction. A preferred curving degree in the head of the sheath tube 13a can be maintained by stopping the rotation of the rotating operation part 11 at a preferred turning angle. Therefore, the curving shape of the head of the sheath tube 13a can be selected according to cases. The sheath tube 13a may uniformly flexible over throughout. However, a flexible part may be placed at the resin of the head end to make only the head end easy to curve.

The medical device 1 described above has the following function effect. Since the first moving member (first slide) 2 and the second moving member (second slide) 4 are placed away from each other, no transmission power is lost by friction generated between the two moving members (slides) 2 and 4. Therefore, since no strong torque transmitting to the rotating operation part (dial) 11 is necessary, the operability when the direction of the head of the sheath tube 13a is controlled can be improved.

As shown in FIGS. 2, 3, and 6 to 8, a ring-shaped concave groove 11b is formed at the base end 11a of the rotating operation part (dial) 11. An O-ring 17 as a friction member is put around the ring-shaped concave groove 11b. Thus, the O-ring 17 is placed around the outer edge of the main gear 10 of the rotating operation part 11. In the assembled medical device 1, the O-ring 17 is placed between the rotating operation part 11 and the handle case 12, which produces frictional force between the rotating operation part 11 and the handle case 12 when the rotating operation part 11 is operated to rotate.

The medical device 1 according to this Embodiment has the following function effect. The O-ring 17 is placed between the rotating operation part (dial) 11 and the handle case 12 as a friction member producing frictional force between the rotating operation part 11 and the handle case 12 when the rotating operation part 11 is operated to rotate. Accordingly, an appropriate load is applied to the operation of the handle 14 to rotate the rotating operation part 11 at an appropriate load not too heavily or lightly. Therefore, the medical device 1 according to this Embodiment can prevent the rotating operation part (dial) 11 from rotating more than the operator's intent and improve the operability to control the direction of the head of the sheath tube 13a.

Figures 9A, 9B, 9C:
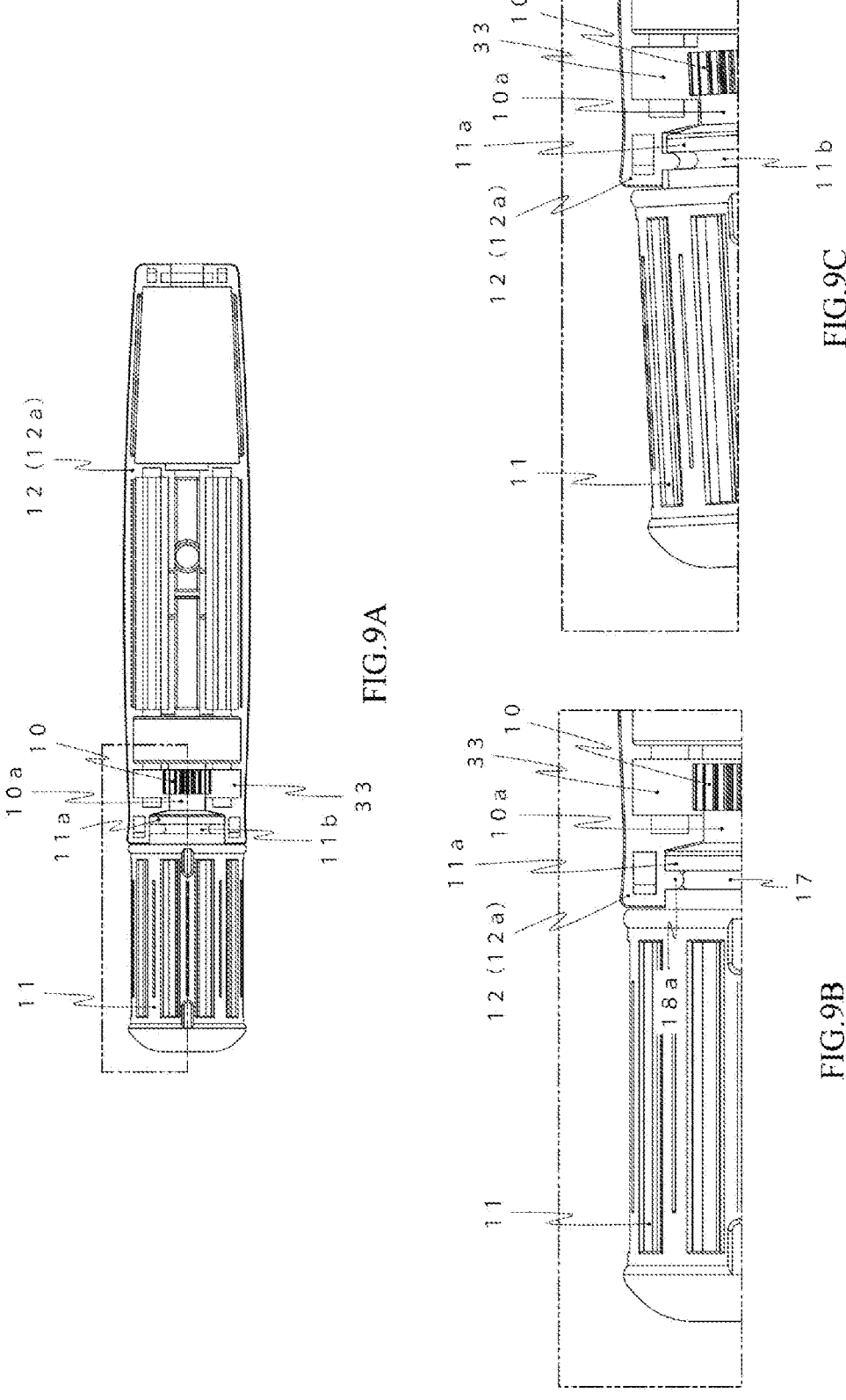
FIGS. 9A-9C are a diagram to explain "how to prevent the components from being dislodged" in the medical device according to Embodiment 1 of the present disclosure.

As shown in FIG. 9C, the rotating operation part (dial) 11 inclines against the handle case 12 if the O-ring 17 as a friction member is not provided. This may be an obstacle to operate the rotating operation part (dial) 11 to smoothly rotate. On the other hand, as shown in FIG. 9B, the rotating operation part (dial) 11 can be prevented from inclining against the handle case 12 if the O-ring 17 as a friction member is provided between the rotating operation part (dial) 11 and the handle case 12. This always enables the rotating operation part (dial) 11 to be operated to smoothly rotate. Moreover, preventing the rotating operation part (dial) 11 from inclining against the handle case 12 contributes to improve "the pushability of the sheath tube 13a" that is described later.

In the medical device disclosed in Patent Document 3, when the rotating operation part (dial) is rotated to make the head curve while a device used in combination is being inserted in a deflectable sheath, power is applied to make the curve part straight by the stiffness of the device used in combination. Therefore, when the operator gets his/her fingers off of the rotating operation part (dial), the rotating operation part (dial) rotates reversely to the neutral position so that the shape of the curve part may not be maintained. Moreover, the same is true in case a device used in combination is inserted after the head of a deflectable sheath is previously curved. When the rotating torque of the rotating operation part (dial) is too weak, the rotating operation part (dial) may rotate reversely even if the device used in combination is not inserted. On the other hand, the medical device 1 according to this Embodiment is provided with the O-ring 17 as a friction member between the rotating operation part (dial) 11 and the handle case 12. When the rotating operation part 11 is operated to rotate, the O-ring 17 produces frictional force between the rotating operation part 11 and the handle case 12. Therefore, the rotating operation part (dial) 11 can be prevented from reversely rotating without the operator's intent.

Figure 6:
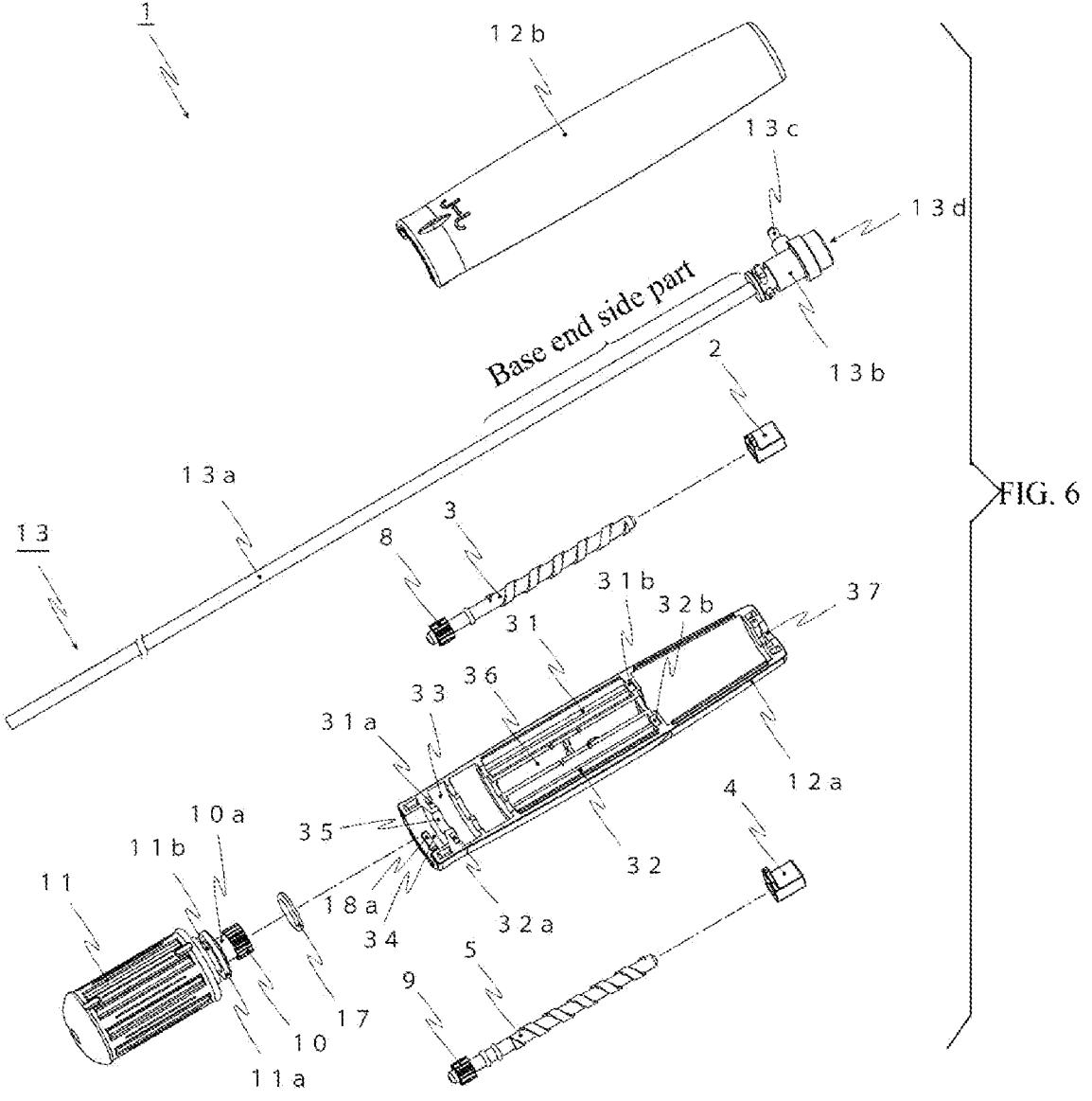
FIG. 6 is an exploded perspective view illustrating the components of the medical device according to Embodiment 1 of the present disclosure. (The first and the second operation wires are omitted.)
Figure 7:
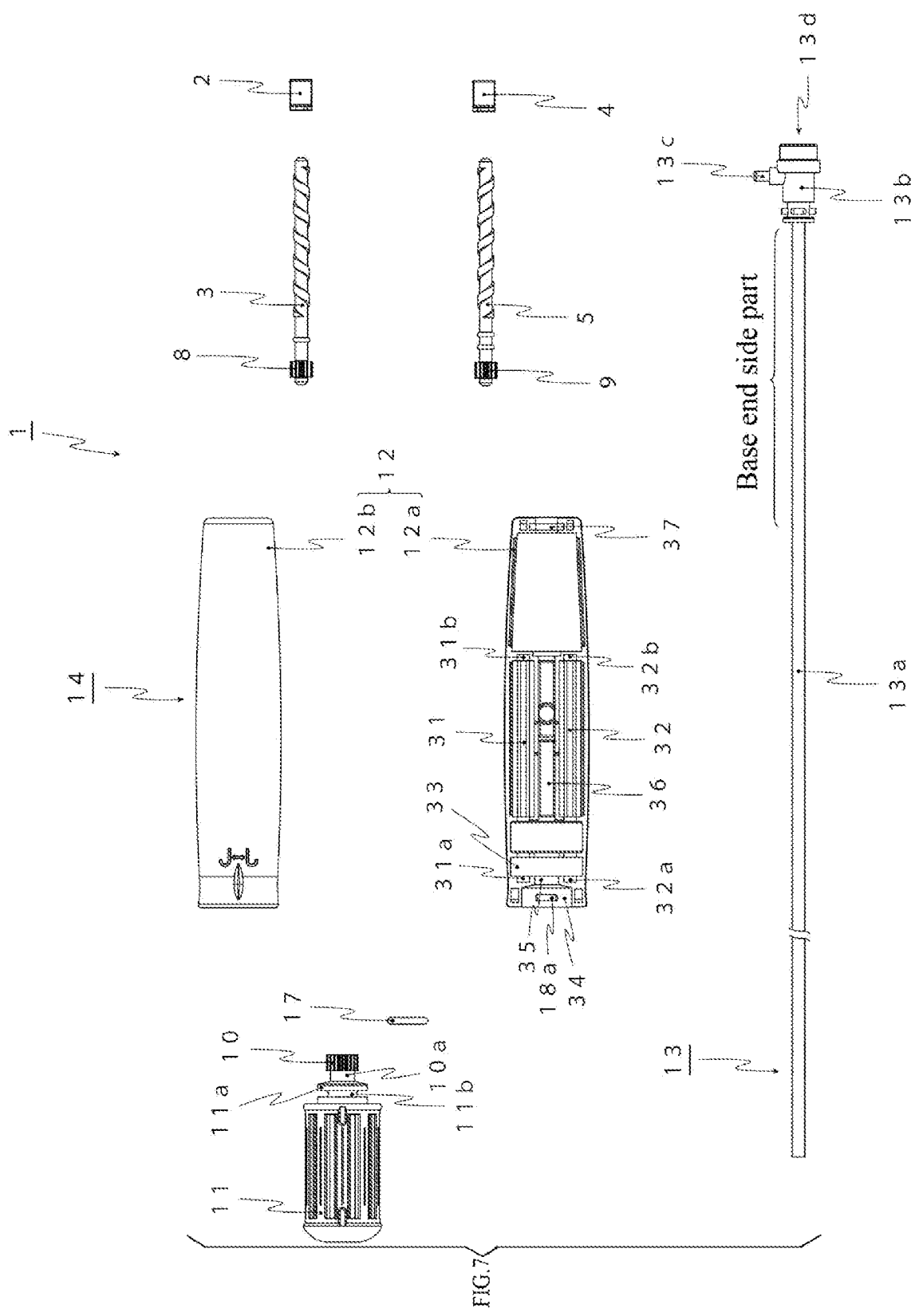
FIG. 7 is an exploded plan view illustrating the components of the medical device according to Embodiment 1 of the present disclosure. The first and the second operation wires are omitted.)
Figure 8:
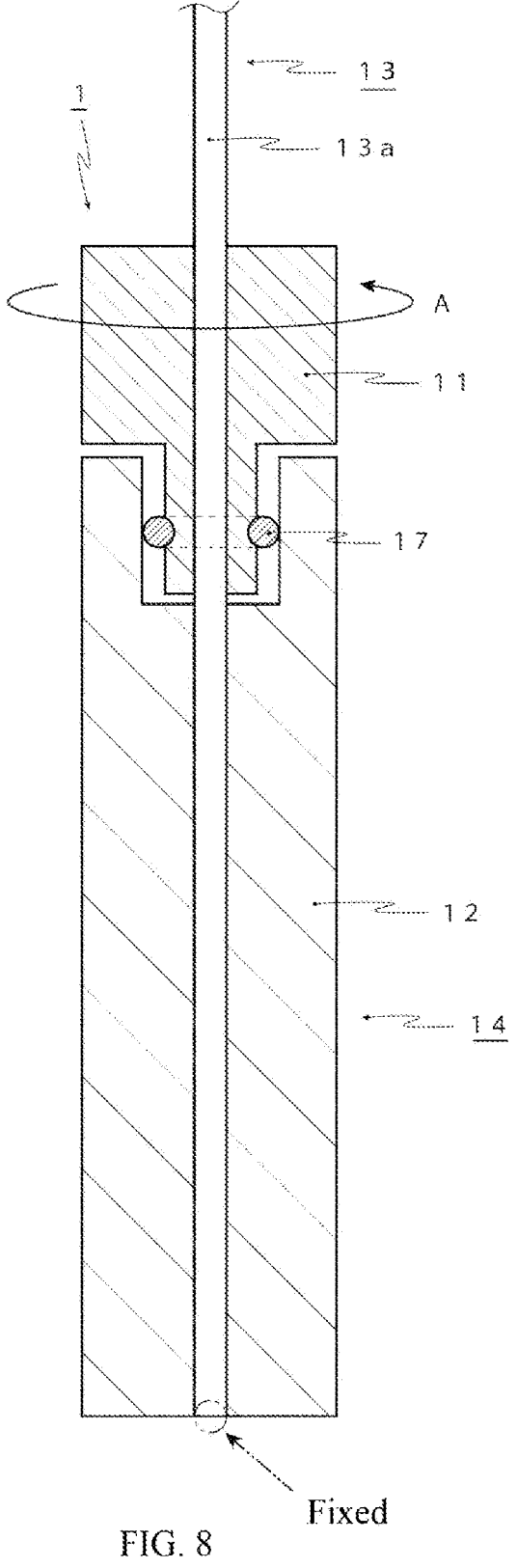
FIG. 8 is a pattern diagram illustrating the situation in which the O-ring is put as a friction member of the medical device according to Embodiment 1 of the present disclosure.

As shown in FIGS. 6 and 7, the first case member 12a and the second case member 12b that compose the handle case 12 are formed in an approximate semicircular column-shape. In the first case member 12a and the second case member 12b, a plurality of similar concaves and bearings are formed. The first case member 12a is explained below, but the second case member 12b is not because the second case member 12b has the same configuration as that of the first case member 12a.

In the first case member 12a, a first feed rod accommodating concave 31 and a second feed rod accommodating concave 32 that accommodates the first feed rod 3 and the second feed rod 5, respectively, are formed. The first feed rod accommodating concave 31 and the second feed rod accommodating concave 32 are formed in parallel at pre-determined intervals along the longitudinal direction of the first case member 12a. The first feed rod accommodating concave 31 and the second feed rod accommodating con-cave 32 have the section crossing the longitudinal direction that is formed in an approximate rectangle-shape to enable the first moving member 2 and the second moving member 4, respectively, to move. In the head end side and the base end side of the first feed rod accommodating concave 31, bearings 31a and 31b that rotatably support the first feed rod 3 are formed. In the head end side and the base end side of the second feed rod accommodating concave 32, bearings 32a and 32b that rotatably support the second feed rod 5 are formed. In the head side of the first case member 12a, a gear accommodating concave 33 that accommodates the first gear 8, the second gear 9, and the main gear 10 engaging with the first gear 8 and the second gear (refer to FIGS. 2 and 3) is formed. In the first case member 12a, a base end accom-modating concave 34 that is located closer to the head side than the gear accommodating concave 33, which accommo-dates the base end 11a of the rotating operation part (dial) 11, and a bearing 35 that rotatably supports the gear axis 10a of the main gear 10 are formed. Moreover, in the first case member 12a, a sheath tube accommodating concave 36 that is located between the first feed rod accommodating concave 31 and the second feed rod accommodating concave 32, which accommodates the base end side part of the sheath tube 13a, is formed. At the base end of the first case member 12a, the head end accommodating concave 37 that accom-modates the sheath hub 13b not rotatably (fixedly, refer to FIG. 8) is formed.

Figure 16:
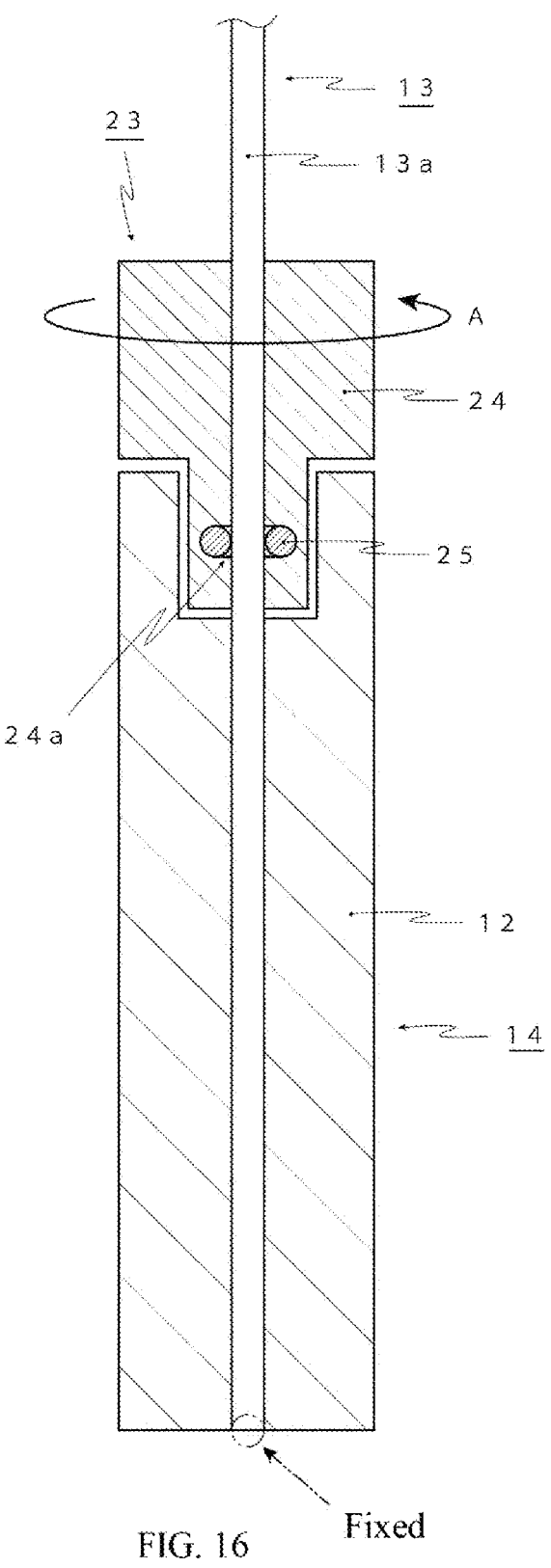
FIG. 16 is a pattern diagram illustrating the second situation in which the O-ring is put as a friction member of the medical device according to Embodiment 1 of the present disclosure.

For the positive handle, the introducer sheath 13 is fixed in the base end side of the handle case 12 as described above. Furthermore, an O-ring as a friction member is placed in the space shared with the sheath tube 13a in the rotating operation part located in the head side of the handle case 12 as described above (refer to FIG. 16 described later). Accordingly, the sheath tube 13a is prevented from twisting in the handle case 12 so that the torque produced by the rotating operation of the handle case 12 can be easily transmitted to the sheath tube 13a (to enhance the torque transmissibility). Therefore, the sheath tube 13a is prevented from twisting by completely matching the rotation of the handle case 12 with that of the sheath tube 13a so that the rotation of the handle case 12 can be directly transmitted to the sheath tube 13a. Moreover, the pushability to certainly transmit pushing force from the operator to the head of the sheath tube 13a can be improved. Therefore, when the handle case 12 is pushed straight, the sheath tube 13a is also pushed straight.

As shown in FIGS. 1 to 3, 6, and 7, a through-hole (not shown) that passes through their common central axis is formed in the rotating operation part 11 and the gear axis 10a of the main gear 10. The sheath tube 13a can be passed through the through-hole.

As shown in FIGS. 4 and 5, in the sheath tube 13a, a first sublumen 13f and a second sublumen 13g are formed, extending from just front of the main gear 10 to the head end in addition to a main lumen 13e that passes the dilator, etc. The first (head) ends of the first operation wire 6 and the second operation wire 7 that pass through the first sublumen 13f and the second sublumen 13g, respectively, are fixed in the head end of the sheath tube 13a by a wire joint ring 15.

As shown in FIGS. 2, 3, 6, and 7, male threads are formed on the first feed rod 3 and the second feed rod 5, which are threaded reversely from each other. Moreover, female threads are formed on the first moving member 2 and the second moving member 4, which are threadably mounted on the first feed rod 3 and the second feed rod 5, respectively. Accordingly, the first feed rod 3 and the second feed rod 5 are rotated in the same direction to enable the first moving member 2 and the second moving member 4, respectively, to move in the directions opposite to each other on the first feed rod 3 and the second feed rod 5, respectively.

Figure 10B:
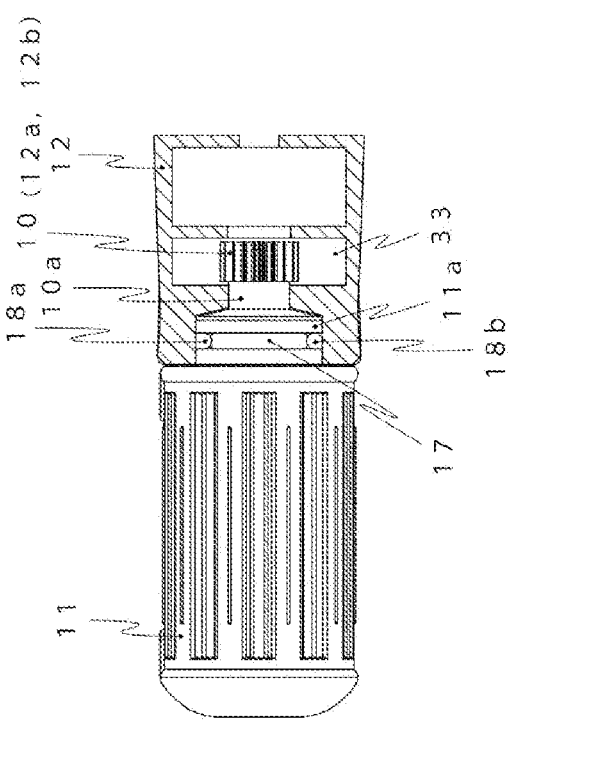
FIGS. 10A-10B are a side view illustrating the position relation between the O-ring as a friction member and the projections of the medical device according to Embodiment 1 of the present disclosure (FIG. 10A is an exploded view, and FIG. 10B is an assembling diagram.)
Figure 10A:
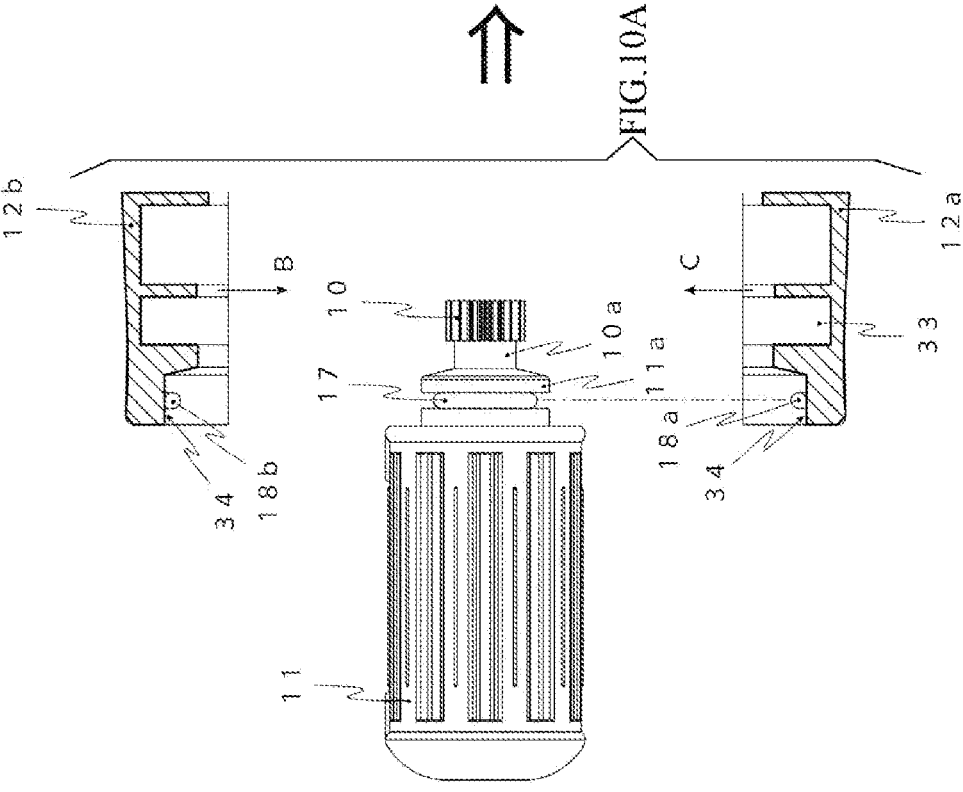
Figures 11A, 11B, 11C:
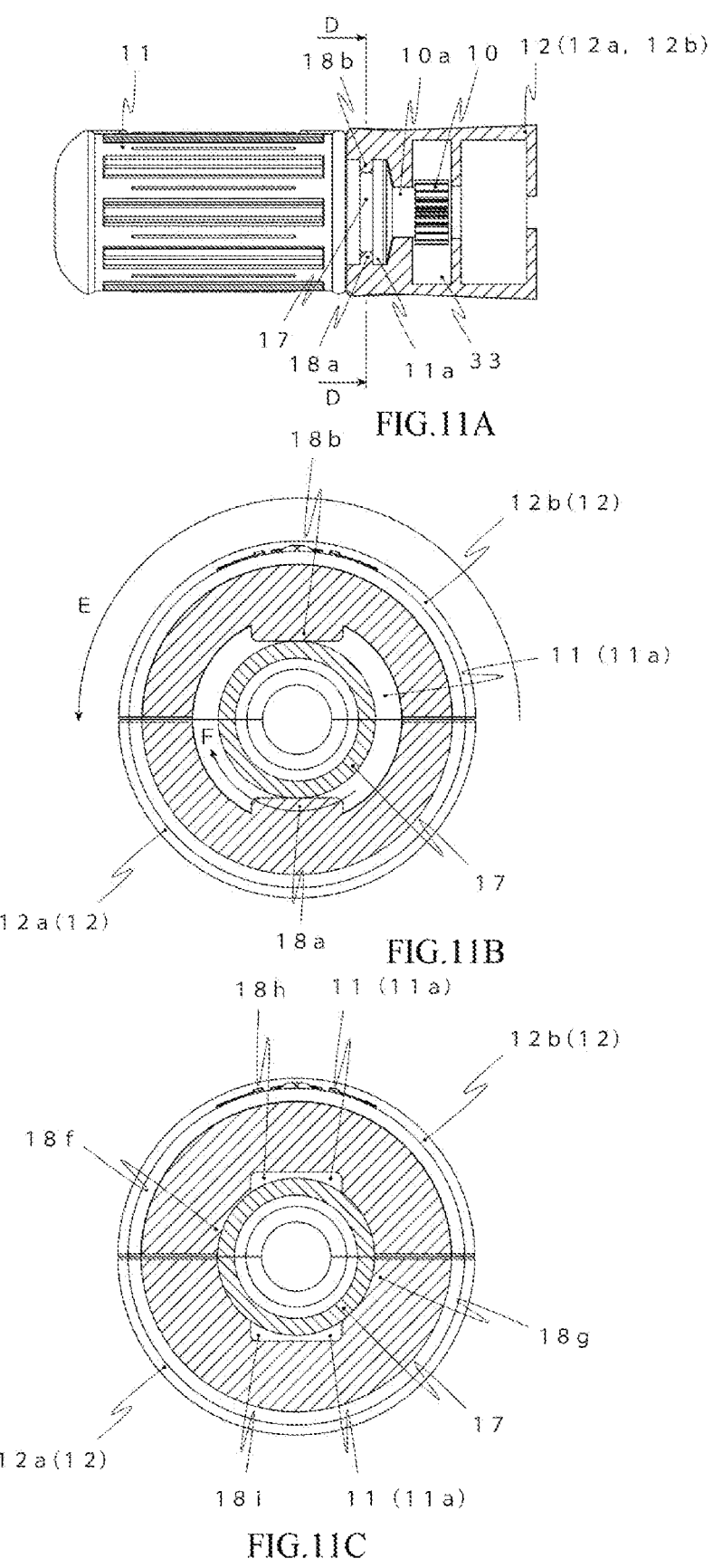
FIGS. 11A-11C are a diagram illustrating the direction of friction produced by the O-ring as a friction member of the medical device according to Embodiment 1 of the present disclosure.

As shown in FIGS. 6, 7, and 10A, projections 18a and 18b that are in contact with the O-ring 17 as a friction member are placed on the inner face of the handle case (gripper) 12. More specifically, the projection 18a is placed in the base end accommodating concave 34 of the first case member 12a that accommodates the base end 11a of the rotating operation part 11, and the projection 18b is placed in the base end accommodating concave 34 of the second case member 12b. Accordingly, the projections 18a and 18b are placed to face each other on the inner face of the handle case (gripper) 12 (refer to FIG. 15B). As shown in FIG. 10B, in the assembled medical device 1 (refer to the arrows B and C of FIG. 10A), the O-ring 17 is in contact with the projections 18a and 18b, which produces frictional force between the O-ring 17 in the rotating operation part 11 side and the projections 18a and 18b in the handle case 12 side when the rotating operation part 11 is operated to rotate. For example, when the rotating operation part (dial) 11 is rotated in a predetermined direction as shown in FIGS. 11A-11C (refer to the arrow E of FIG. 11B), frictional force is produced in a direction opposite to the rotation direction (circumferential direction) of the rotating operation part 11 between the O-ring 17 in the rotating operation part 11 side and the projections 18a and 18b in the handle case 12 side (refer to the arrow F of FIG. 11B).

Accordingly, an appropriate load is applied to the rotating operation of the rotating operation part 11 to rotate the rotating operation part 11 at an appropriate load not too heavily or lightly. As the result, the rotating operation part (dial) 11 is prevented from rotating more than the operator's intent to enable the head of the sheath tube 13a to be avoided from bending too much or too little so that the head of the sheath tube 13a can be formed in a curve shape that the operator intends. Therefore, the operability when the direc-tion of the head of the sheath tube 13a is controlled can be more improved. Especially, the projections 18a and 18b that are in contact with the O-ring 17 as a friction member are placed on the inner face of the handle case 12 so that a constant brake can be applied to the rotation of the rotating operation part 11 by adjusting the frictional force between the rotating operation part 11 and the handle case 12.

The length in the circumferential direction of the projec-tions is not limited in particular as long as the frictional force between the rotating operation part 11 and the handle case 12 reaches an appropriate amount. For example, the projections 18f and 18g may lengthened in the circumferential direction, and the dents 18h and 18i may be placed in the part not contacting the O-ring 17 as shown in FIG. 11C. Accordingly, the head of the sheath tube 13a can be avoided from bending too much or too little so that the head of the sheath tube 13a can be formed in a curve shape that the operator intends.

Figures 12A, 12B, 12C:
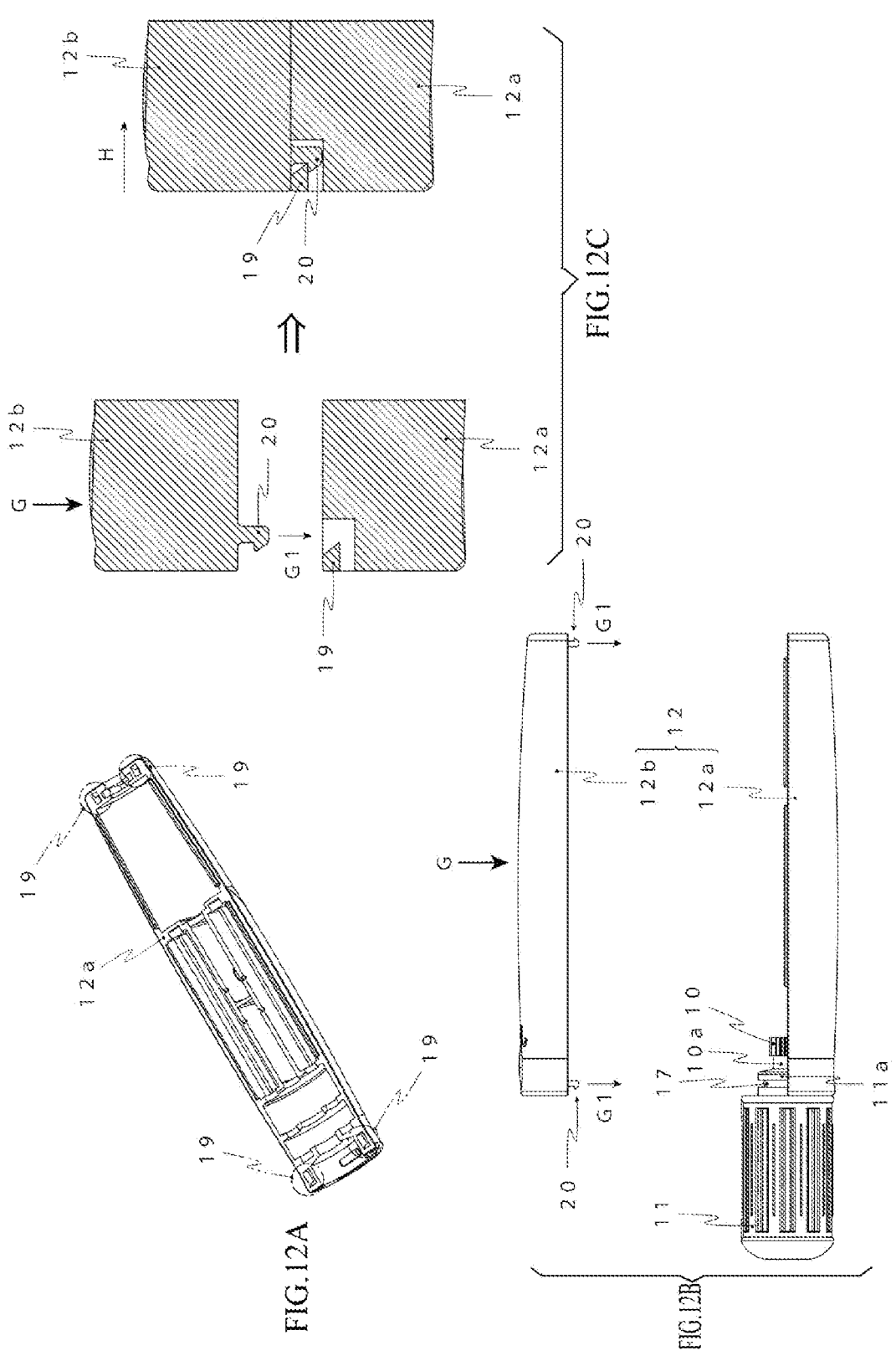
FIGS. 12A-12C are a diagram to explain how to assemble and disassemble the gripper (handle case) of the medical device according to Embodiment 1 of the present disclosure.

As shown in FIGS. 12A and 12B, a first tab 19 that faces inward in the longitudinal direction of the first case member 12a is formed at the four corners on the face of the first case member 12a that is opposite to the second case member 12b. A second tab 19 that is engageable with the first tab 19 is formed at the four corners on the face of the second case member 12b that is opposite to the first case member 12a. As shown in FIGS. 12B and 12C, the first case member 12a and the second case member 12b face each other, and then the second tab 20 is set in and engaged with the first tab 19 (refer to the arrow G1 of FIGS. 12B and 12C) by depressing the second case member 12*b* from up above (refer to the arrow G of FIGS. 12B and 12C) to integrate the first case member 12*a* with the second case member 12*b* (in a set-in way). The second tab 20 can be removed from the first tab 19 by turning the one of the edges of the second case member 12*b* to the head of the longitudinal direction (the direction of the arrow H of FIG. 12C) and depressing it. As the result, the second case member 12*b* can be detached from the first case member 12*a*. (The handle case 12 can be disassembled). Thus, the first case member 12*a* and the second case member 12*b* are detachably integrated with each other. Accordingly, the medical device 1 can be easily disassembled. Therefore, the handle (rotating operation part (dial) 11+handle case 12) 14 is easily recycled, and the medical device using the handle 14 can be reproduced. To remove the second tab 20 from the first tab 19, a pin may be inserted in a hole that opens on the side of the first tab 19 to disengage the first tab 19 from the second tab 20.

Use of Medical Device

The use of the medical device according to Embodiment 1 of the present disclosure is described below with reference to FIGS. 13A-13B and 14A-14B.

The medical device 1 is used integrally with a dilator, for example, when a cardiac catheter is inserted from a blood vessel (great vein) in the atria.

Heparin saline is injected from the three way cock into the sheath tube 13*a* before the sheath tube 13*a* is inserted into a blood vessel. After access to the femoral vein is secured, a guide wire is inserted in the precaval vein, and the dilator and the sheath tube 13*a* are inserted along the guide wire. When the head of the dilator reaches the precaval vein, the guide wire is removed, and then the septum needle is inserted into the sheath tube 13*a*. After the atrial septum is punctured with the septum needle, and the dilator and the sheath tube 13*a* are put forward in the left atria, the dilator is pulled out, and the cardiac catheter is inserted and placed at an intended site.

If necessary, the rotating operation part (dial) 11 is rotated to deflect the head of the sheath tube 13*a* and adjust the indwelling site of the cardiac catheter. For example, when the handle case 12 is gripped in one hand, and the rotating operation part 11 is rotated in a positive rotation direction in the other hand as shown in FIGS. 13A-13B (refer to the arrow A of FIG. 13A), the first feed rod 3 and the second feed rod 5 rotate in the same direction (negative rotation direction) through the main gear 10, the first gear 8, and the second gear 9. Then, the first moving member 2 moves to the base end side (refer to the arrow I of FIG. 13A), and the second moving member 4 moves to the head side (refer to the arrow J of FIG. 13A). As the result, the first operation wire 6 is pulled to the base end side, the second operation wire 7 is loosened (refer to FIG. 5), and the head of the sheath tube 13*a* is deflected in the first direction toward the side (side port 13*c* side) from which the side tube comes out (refer to arrow K of FIG. 13B).

Figures 14A, 14B:
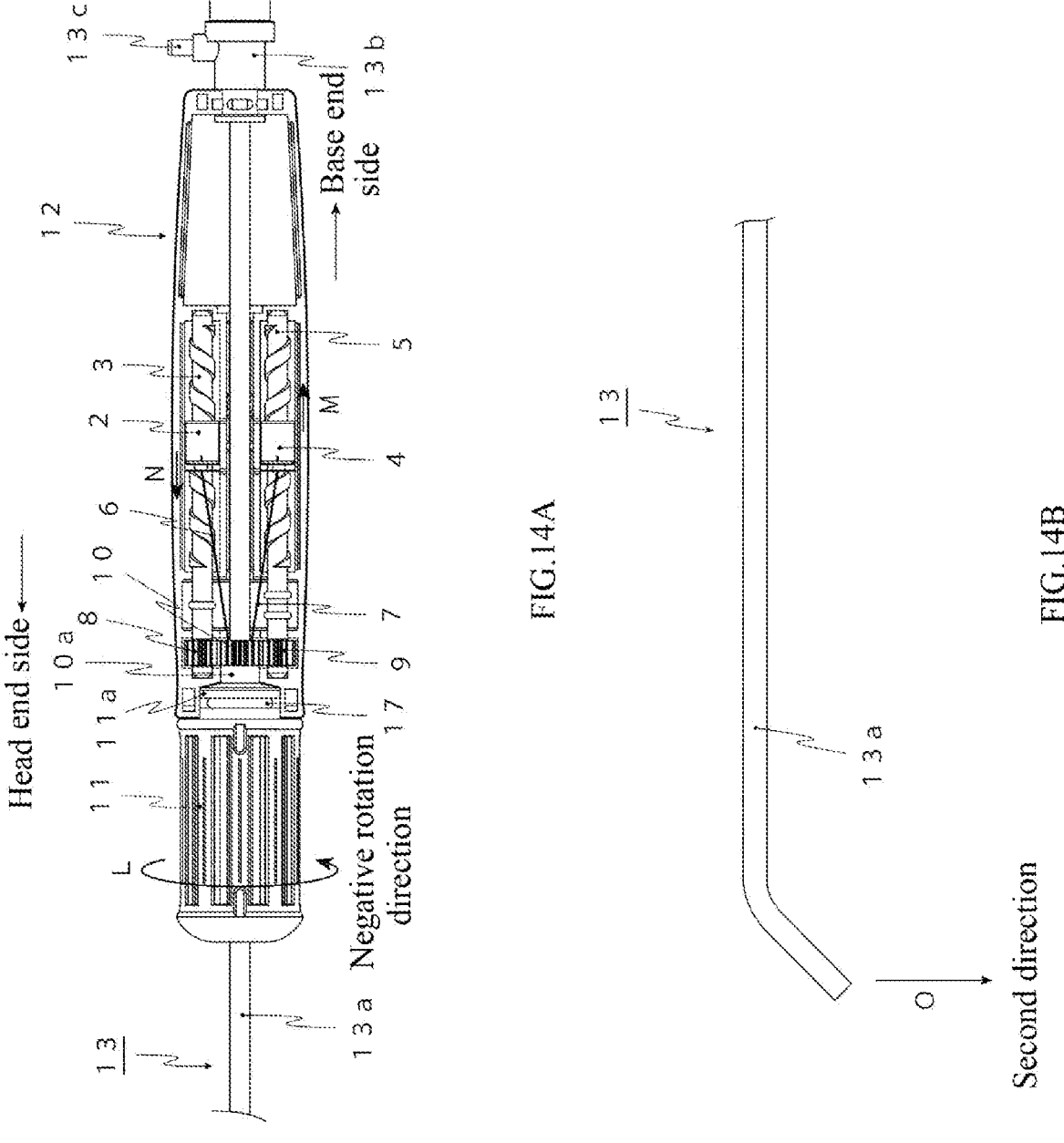
FIGS. 14A-14B are a plan view illustrating the second example use of the medical device according to Embodiment 1 of the present disclosure.

For example, when the handle case 12 is gripped in one hand, and the rotating operation part 11 is rotated in the negative rotation direction in the other hand as shown in FIGS. 14A-14B (refer to the arrow L of FIG. 14A), the first feed rod 3 and the second feed rod 5 rotate in the negative direction through the main gear 10, the first gear 8, and the second gear 9. Then, the second moving member 4 moves to the base end side (refer to the arrow M of FIG. 14A), and the first moving member 2 moves to the head side (refer to the arrow N of FIG. 14A). As the result, the second operation wire 7 is pulled to the base end side, the first operation wire 6 is loosened (refer to FIG. 5), and the head of the sheath tube 13*a* is deflected in the second direction toward the side opposite to the side (side port 13*c* side) from which the side tube comes out (refer to arrow O of FIG. 14B).

Accordingly, since the indwelling site of the cardiac catheter can be adjusted, the cardiac catheter can be placed at an intended site correctly. The deflecting direction has been explained, giving an example of the side (side port 13*c* side) from which the side tube comes out. However the deflecting direction of the present disclosure is not limited to the basis of such an example. The head of the sheath tube 13*a* only has to deflect in the opposite direction.

As described above, when the atrial septum is punctured with the septum needle, and the dilator and the sheath tube 13*a* are put forward in the left atrium, the sheath tube 13*a* is screwed to puncture the atrial septum through without curving the head of the sheath tube 13*a*. As described above, the medical device 1 according to this Embodiment can increase the torque transmissibility, the atrial septum can be efficiently punctured with the septum needle, and the dilator and the sheath tube 13*a* are efficiently put forward in the left atria.

This Embodiment has been explained, giving an example where the introducer sheath 13 is used for inserting a cardiac catheter from a blood vessel into the atrium and ventricles as the tubular member. However, the present disclosure is not necessarily limited to such an example. The tubular member may be another tubular member for a catheter, an endoscope, etc., as long as it has flexibility.

Figures 15A, 15B, 15C, 15D:
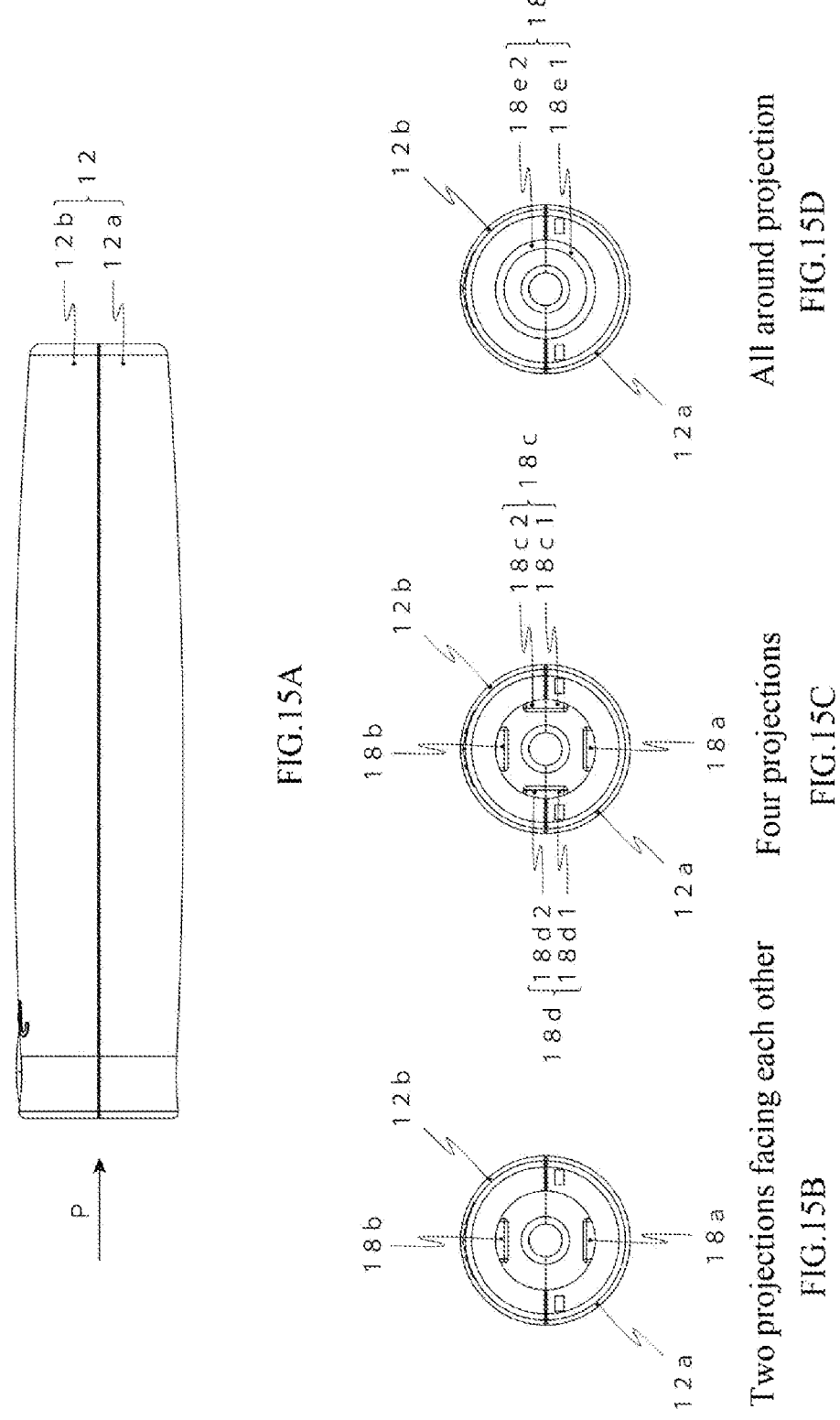
FIGS. 15A-15D are a diagram illustrating a variation of the projections of the medical device according to Embodiment 1 of the present disclosure.

This Embodiment has been explained, giving an example where the two projections 18*a* and 18*b* are placed to face each other on the inner face of the handle case (gripper) 12 to make contact with the O-ring 17 (refer to FIG. 15B). However, the present disclosure is not necessarily limited to such an example. For example, the four projections 18*a*, 18*b*, 18*c*, and 18*d* may be placed on the inner face of the handle case 12 to make contact with the O-ring 17 as shown in FIG. 15C. In this case, the projections 18*a*, 18*c*, 18*b*, and 18*d* are placed in the circumferential direction at intervals of approximate 90 degrees. The projection 18*c* is composed of a projection 18*c*1 placed in the first case member 12*a* side and a projection 18*c*2 placed in the second case member 12*b* side, and the projection 18*d* is composed of a projection 18*d*1 placed in the first case member 12*a* side and a projection 18*d*2 placed in the second case member 12*b* side. Moreover, a ring-shaped projection 18*e* that is in contact with the O-ring 17 may be placed all around on the inner face of the handle case (gripper) 12 as shown in FIG. 15D, for example. In this case, the projection 18*e* is composed of a semi-ring shaped projection 18*e*1 placed in the first case member 12*a* side and a semi-ring shaped projection 18*c*2 placed in the second case member 12*b* side. The above-mentioned variation of the number of the projections enables the frictional force between the rotating operation part 11 and the handle case 12 to be adjusted.

This Embodiment has been explained, giving an example where the O-ring 17 as a friction member is placed around the outer edge of the main gear 10 of the rotating operation part (dial) 11. However, the present disclosure is not necessarily limited to such an example. Other examples are explained below with reference to FIGS. 16 to 18. In the medical device 23 shown in FIG. 16, the O-ring 25 as a friction member is placed in the space shared with the sheath tube 13*a* in the rotating operation part (dial) 24. Specifically, in the rotating operation part (dial) 24, a ring-shaped concave groove 24*a* that is communicated with a through-hole passing through the sheath tube 13*a* is formed. The O-ring 25 as a friction member is put around the concave groove 24*a*. In the assembled medical device 23, the O-ring 25 is placed between the rotating operation part 24 and the sheath tube 13*a*, which produces frictional force between the rotating operation part 24 and the sheath tube 13*a* when the rotating operation part 24 is operated to rotate (for example, refer to the arrow A of FIG. 16).

The medical device 23 of this example has the following function effect. The O-ring 25 is placed between the rotating operation part (dial) 24 and the sheath tube 13*a* as a friction member producing frictional force between the rotating operation part 24 and the sheath tube 13*a* when the rotating operation part 24 is operated to rotate. Accordingly, an appropriate load is applied to the operation of the handle 14 to rotate the rotating operation part 24 at an appropriate load not too heavily or lightly. Therefore, the medical device 23 can prevent the rotating operation part (dial) 24 from rotating more than the operator's intent and improve the operability to control the direction of the head of the sheath tube 13*a*.

For the positive handle, the introducer sheath 13 is fixed in the base end side of the handle case 12. Furthermore, an O-ring 25 as a friction member is placed in the space shared with the sheath tube 13*a* in the rotating operation part 24 located in the head side of the handle case 12. Accordingly, the sheath tube 13*a* is prevented from twisting in the handle case 12 so that the torque produced by the rotating operation of the handle case 12 can be easily transmitted to the sheath tube 13*a* (to enhance the torque transmissibility). Therefore, the sheath tube 13*a* is prevented from twisting by completely matching the rotation of the handle case 12 with that of the sheath tube 13*a* so that the rotation of the handle case 12 can be directly transmitted to the sheath tube 13*a*. Moreover, the pushability to certainly transmit pushing force from the operator to the head of the sheath tube 13*a* can be improved. Therefore, when the handle case 12 is pushed straight, the sheath tube 13*a* is also pushed straight.

Figure 17:
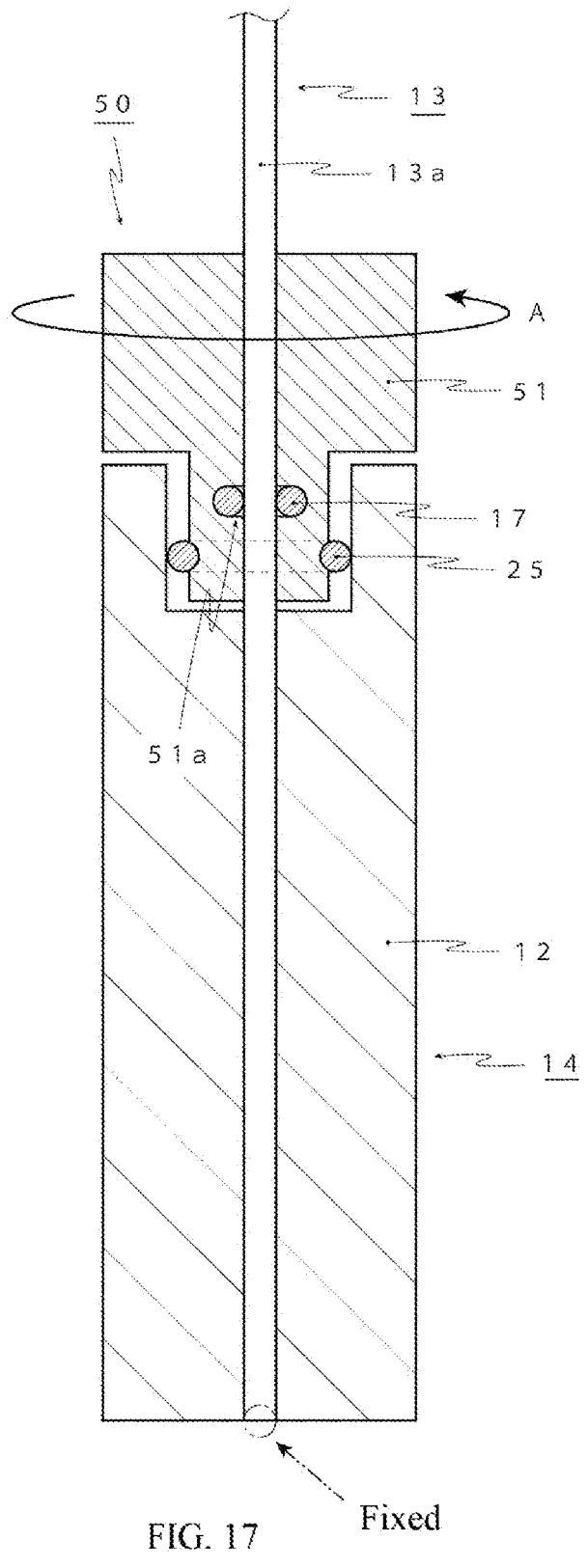
FIG. 17 is a pattern diagram illustrating the third situation in which the O-ring is put as a friction member of the medical device according to Embodiment 1 of the present disclosure.

In the medical device 50 shown in FIG. 17, the O-ring 25 as a friction member is put around the outer edge of the main gear of the rotating operation part (dial) 51, and the O-ring 17 as a friction member is placed in the space shared with the sheath tube 13*a* in the rotating operation part (dial) 51. Specifically, in the rotating operation part (dial) 51, a ring-shaped concave groove 51*a* that is communicated with a through-hole passing through the sheath tube 13*a* is formed. The O-ring 17 as a friction member is put around the concave groove 51*a*. In the assembled medical device 50, the O-ring 25 is placed between the rotating operation part 51 and the handle case (gripper) 12, which produces frictional force between the rotating operation part 51 and the handle case 12 when the rotating operation part 51 is operated to rotate (for example, refer to the arrow A of FIG. 17). The O-ring 17 is placed between the rotating operation part 51 and the sheath tube 13*a*, which produces frictional force between the rotating operation part 51 and the sheath tube 13*a* when the rotating operation part 51 is operated to rotate (for example, refer to the arrow A of FIG. 17).

The medical device 50 of this example has the function effect similar to those produced by the medical devices 1 and 23.

Figure 18:
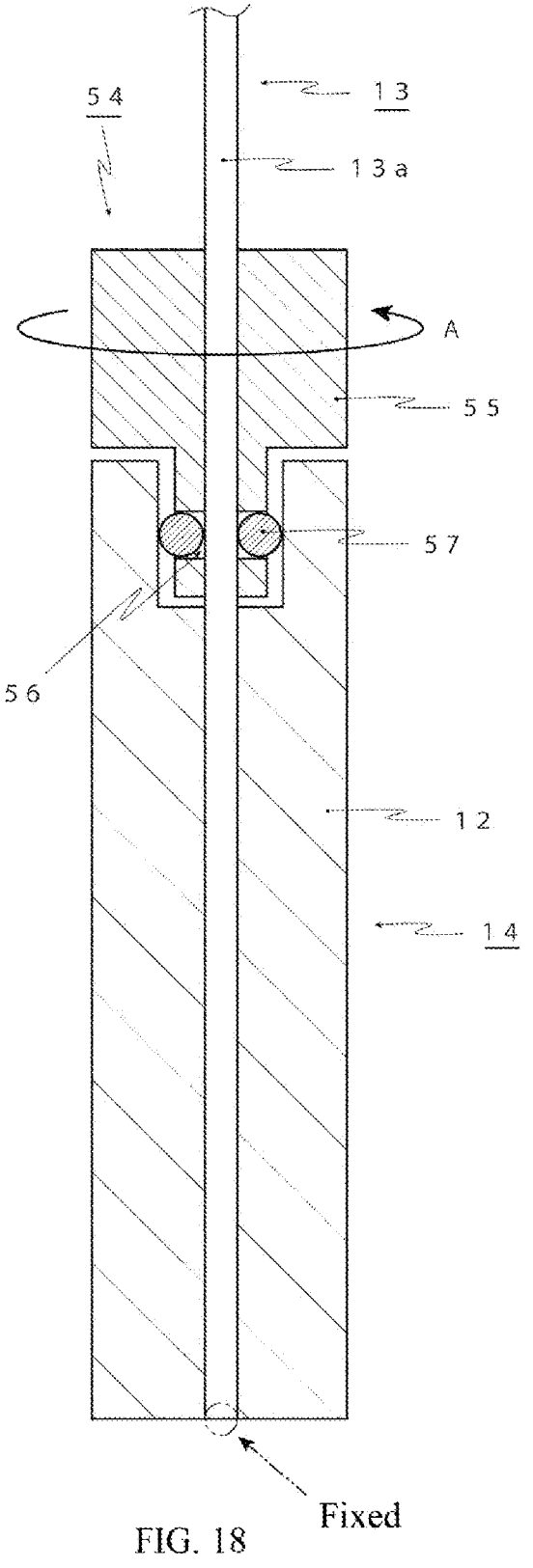
FIG. 18 is a pattern diagram illustrating the fourth situation in which the O-ring is put as a friction member of the medical device according to Embodiment 1 of the present disclosure.

In the medical device 54 shown in FIG. 18, the O-ring 57 as a friction member is put around the outer edge of the main gear of the rotating operation part (dial) 55, and a window 56 is placed in multiple places in the sheath tube 13*a* side. In the assembled medical device 54, the O-ring 57 is placed between the rotating operation part 55 and the handle case (gripper) 12, which produces frictional force between the rotating operation part 55 and the handle case 12 when the rotating operation part 55 is operated to rotate (for example, refer to the arrow A of FIG. 18). The O-ring 57 comes out from the window 56 at multiple places to the sheath tube 13*a* side, which produces frictional force between the rotating operation part 55 and the sheath tube 13*a* when the rotating operation part 55 is operated to rotate (for example, refer to the arrow A of FIG. 18).

The medical device 54 of this example has the function effect similar to that produced by the medical device 1.

Furthermore, this Embodiment has been explained, giving an example where the O-ring 17 is used as a friction member. However, the present disclosure is not necessarily limited to such an example. As a friction member other than the O-ring, for example, a C-ring, an O-ring with bumps and dips in the circumferential direction, gel, fluid, and particles can be used.

Furthermore, this Embodiment has been explained, giving an example where the first case member 12*a* and the second case member 12*b* are set and detachably integrated with each other in set-in way. However, the present disclosure is not necessarily limited to such an example. The first case member 12*a* and the second case member 12*b* may be screwed and detachably integrated with each other.

Embodiment 2

Figures 19A, 19B:
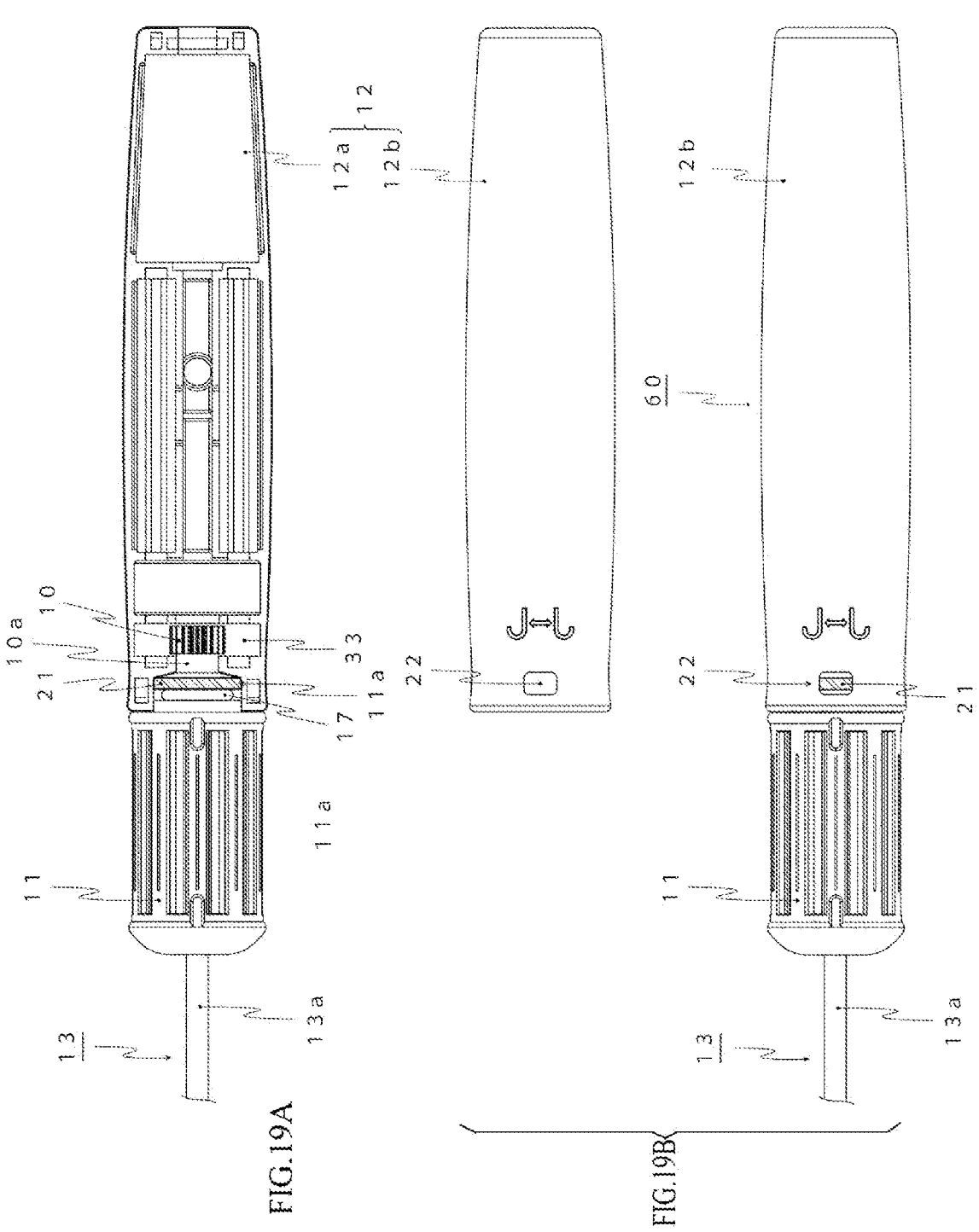
FIGS. 19A-19B are a plan view illustrating the medical device according to Embodiment 2 of the present disclosure (FIG. 19A shows the situation in which the second case member is detached, and FIG. 19B shows the situation in which the second case member is attached.)

The configuration of the medical device according to Embodiment 2 of the present disclosure is described below with reference to FIGS. 19A-19B.

The basic structure and the operating principle of the medical device 60 according to this Embodiment are similar to those of the medical device 1 according to the above-mentioned Embodiment 1. Therefore, the same reference numerals are used to refer the same members as those according to Embodiment 1, and the detailed explanations are omitted. Moreover, the components not related to the explanation are omitted in FIGS. 19A-19B.

The difference from the medical device 1 according to the above-mentioned Embodiment 1 is that an indicator is provided. As shown in FIGS. 19A-19B, the base end 11*a* accommodated in the base end accommodating concave 34 (refer to FIGS. 6 and 7) of the handle case (gripper) 12 in the rotating operation part (dial) 11 is marked with a scale 21 that indicates the turning angle of 0° to 180° of the head of the sheath tube 13*a* along the circumferential direction. Moreover, a window 22 through which the scale 21 can be seen from outside is provided in the first case member 12*a* to correspond to the scale 21 in the base end 11*a* of the rotating operation part (dial) 11. Specifically, the scale 21 showing 0° indicates that the rotating operation part (dial) 11 is at the neutral position where the head of the sheath tube 13*a* is straight. The scale 21 showing 30°, 60°, 90°, 120°, and 180°, for example, indicates that the rotating operation part (dial) 11 is rotated 30°, 60°, 90°, 120°, and 180°, respectively, from the neutral position. As the angle indicated by the scale 21 increases, the turning angle in the head of the sheath tube 13*a* increases.

According to the medical device 60 according to this Embodiment, the turning angle of the head of the sheath tube 13*a* can be accurately controlled when the operator operates the rotating operation part (dial) 11 to rotate, watching "the scale 21 indicating the turning angle of 0° to 180° of the head of the sheath tube 13*a*".

This Embodiment has been explained, giving an example where, the base end 11*a* accommodated in the base end accommodating concave 34 of the handle case (gripper) 12 in the rotating operation part (dial) 11 is marked with a scale 21 that indicates the turning angle of 0° to 180° of the head of the sheath tube 13*a* along the circumferential direction. However, the present disclosure is not necessarily limited to such an example. For example, two or more types of colors and pictures (of the bending head of the tubular member) that indicate the turning angle of the head of the sheath tube 13*a* (tubular member) may be painted along the circumferential direction in the base end 11*a* of the rotating operation part (dial) 11.

Embodiment 3

Configuration of Medical Device

The configuration of the medical device according to Embodiment 3 of the present disclosure is described below with reference to FIGS. 5 and 20 to 26, giving an example where the tubular member is an introducer sheath.

Figure 20:
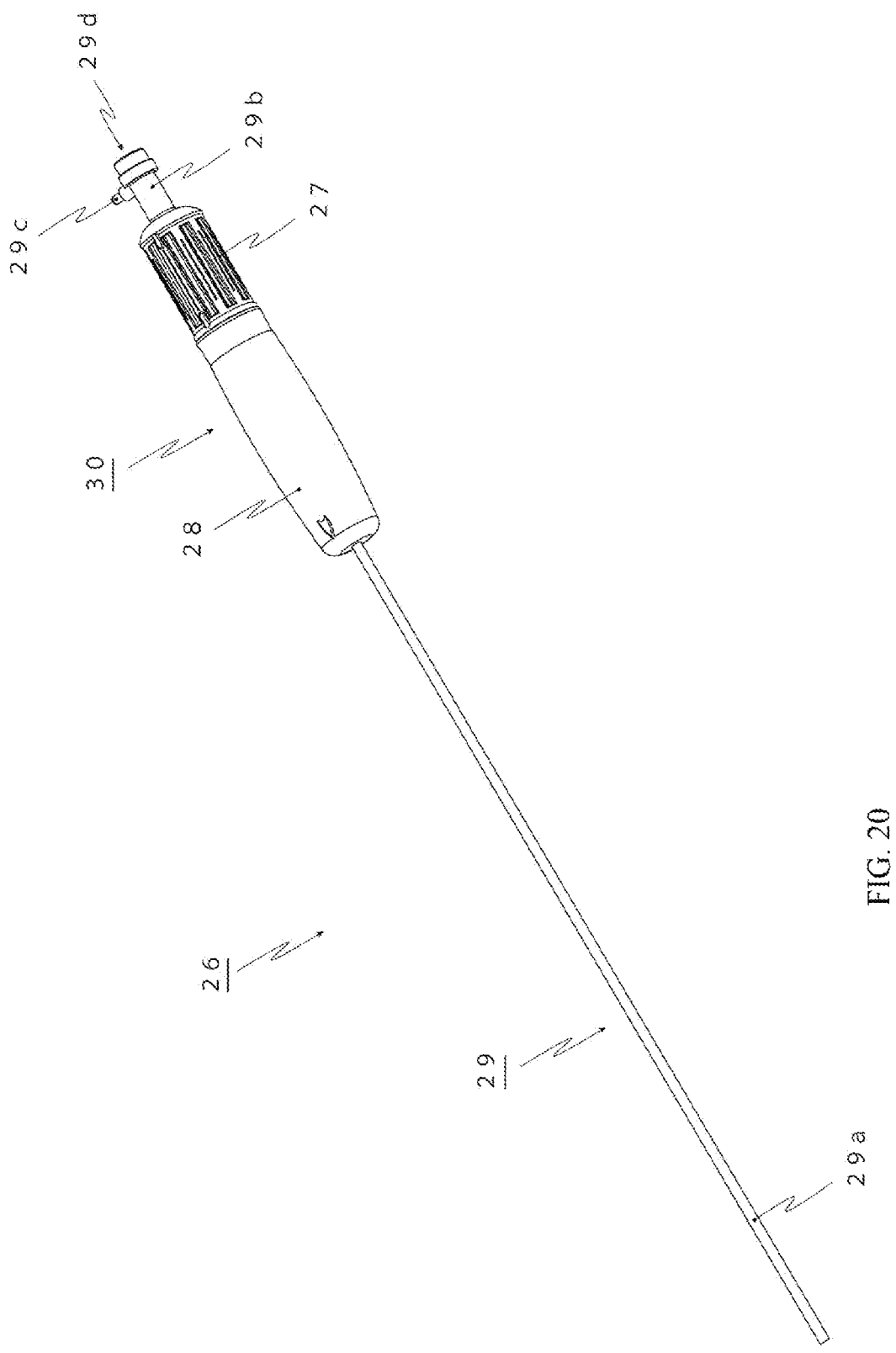
FIG. 20 is a perspective view illustrating the configuration of the medical device according to Embodiment 3 of the present disclosure.
Figure 21:
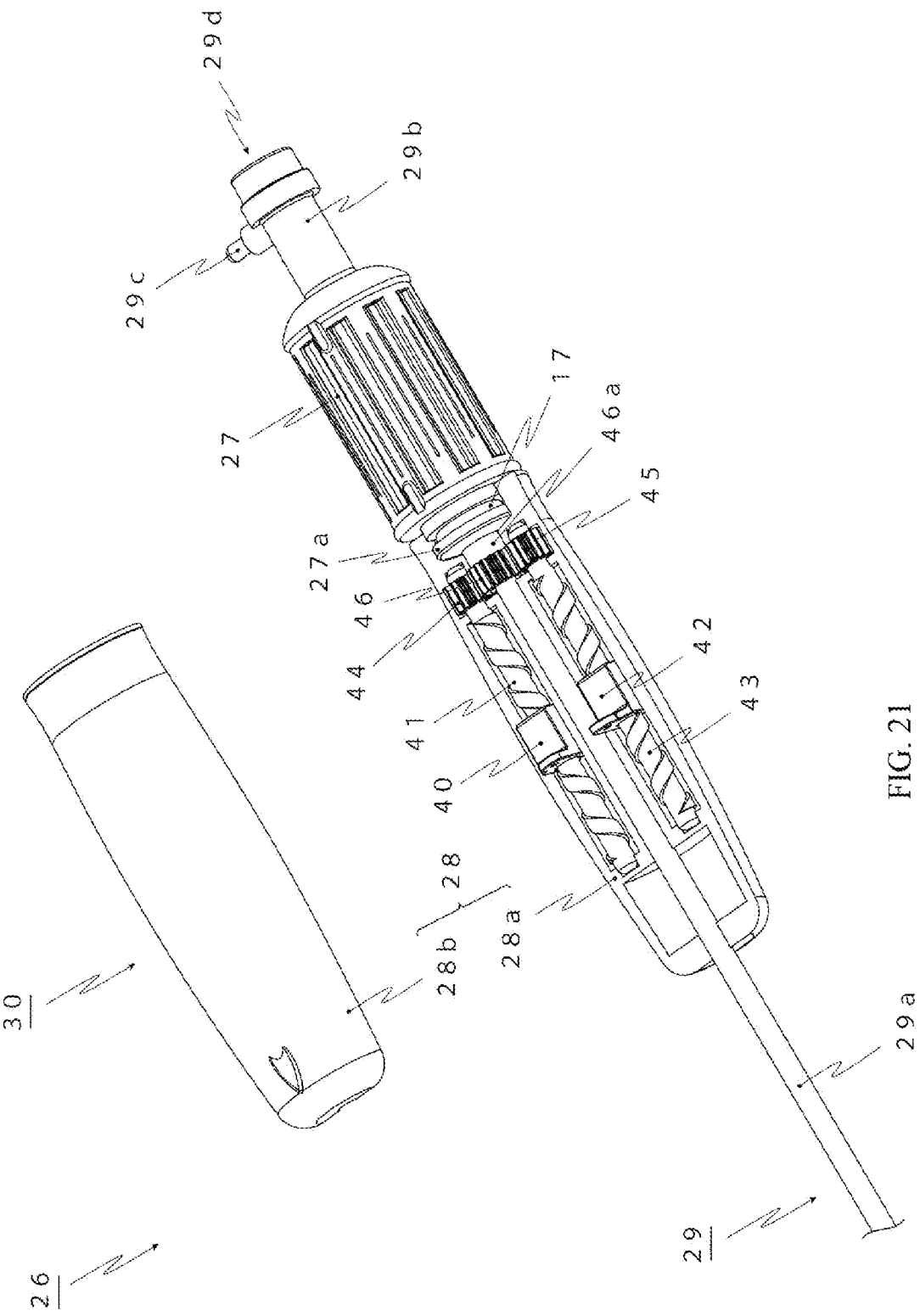
FIG. 21 is a perspective view illustrating an internal mechanism of the medical device according to Embodiment 3 of the present disclosure. (The second case member is detached, and the first and the second operation wires are omitted.)
Figure 22:
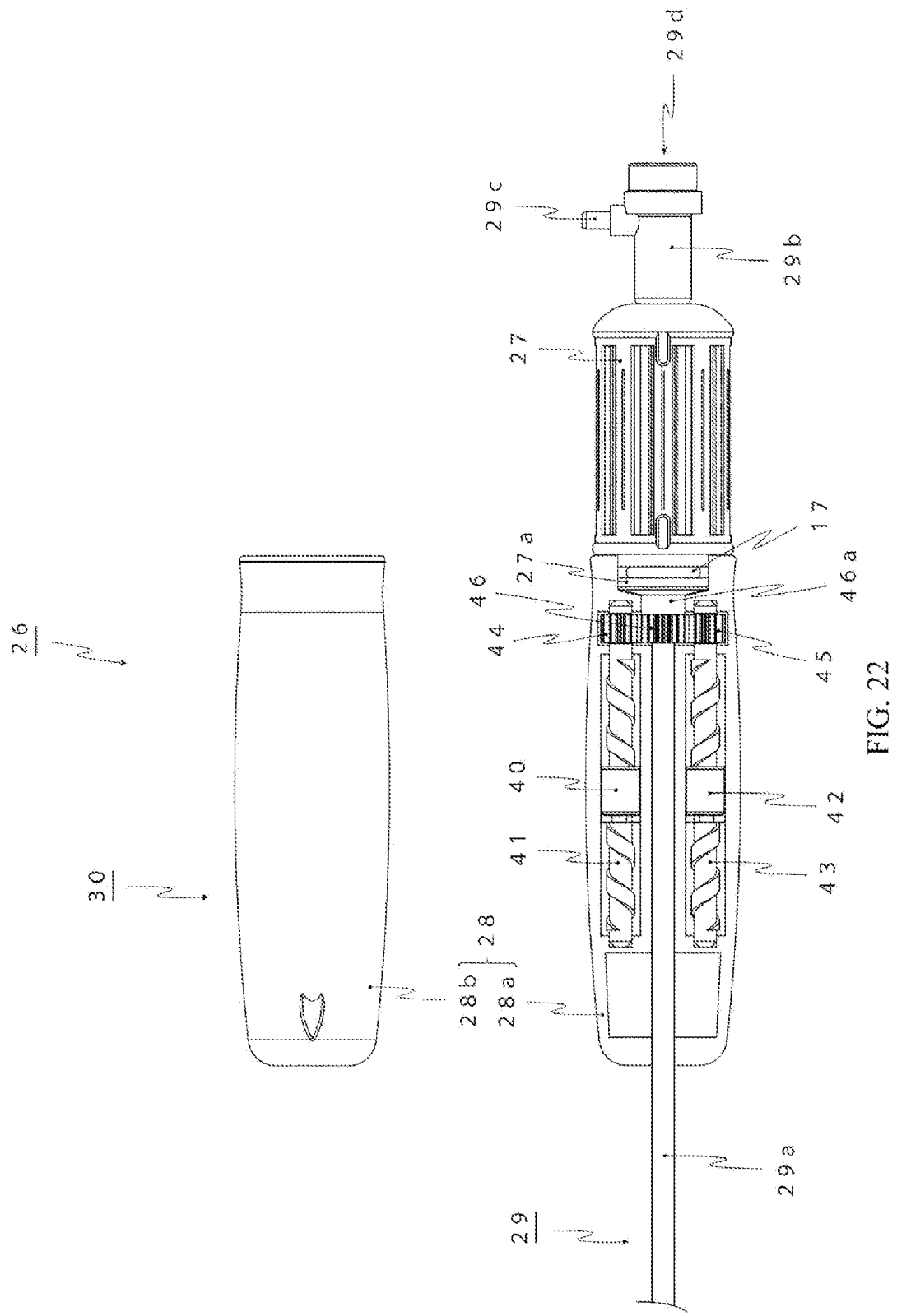
FIG. 22 is a plan view illustrating an internal mechanism of the medical device according to Embodiment 3 of the present disclosure. (The second case member is detached, and the first and the second operation wires are omitted.)

The medical device 26 shown in FIG. 20 is provided with an introducer sheath 29 as a flexible tubular member and a handle 30 that controls the direction of the head of the sheath 29. The sheath 29 is provided with a sheath tube 29*a*, a sheath hub 29*b*, a hemostasis valve (not shown), a side port 29*c*, and a dilator insertion opening 29*d* in the same way as the sheath 13 of above-mentioned Embodiment 1.

As shown in FIGS. 20 to 22, 24, and 25, the handle 30 is provided with a rotating operation part (dial) 27 at the base end and an approximately column-shaped handle case (gripper) 28 at the front end (negative handle). The rotating operation part (dial) 27 is formed in an approximate column-shape, the diameter of which is approximately equal to that of the handle case 28, which rotates the main gear 46 described later. The handle case 28 is formed by mutually assembling an approximately semicircular column-shaped first case member (first gripper member) 28*a* and an approximately semicircular column-shaped second case member (second gripper member) 28*b* that are placed opposite to each other. The handle case 28 accommodates a first moving member 40, a first feed rod 41, a second moving member 42, a second feed rod 43, a first gear 44, a second gear 45, and a main gear 46 in the same way as the handle case 12 according to the above-mentioned Embodiment 1. The first moving member 40 is formed in an approximate cuboid-shape, which moves on the first feed rod 41 in the longitudinal direction. The second moving member 42 is formed in an approximate cuboid-shape, which moves on the second feed rod 43 in the longitudinal direction. The first feed rod 41 and the second feed rod 43 are arranged at intervals of approximate 180 degrees in circumferential direction and accommodated away from each other in the same way of the first feed rod 3 and the second feed rod 5 according to the above-mentioned Embodiment 1. The first gear 44 is fixed at the back end of the first feed rod 41. The second gear 45 is fixed at the back end of the second feed rod 43. The main gear 46 is placed between the first gear 44 and the second gear 45, which transmits rotary driving force in the same direction as those of the first gear 44 and the second gear 45.

Figure 23:
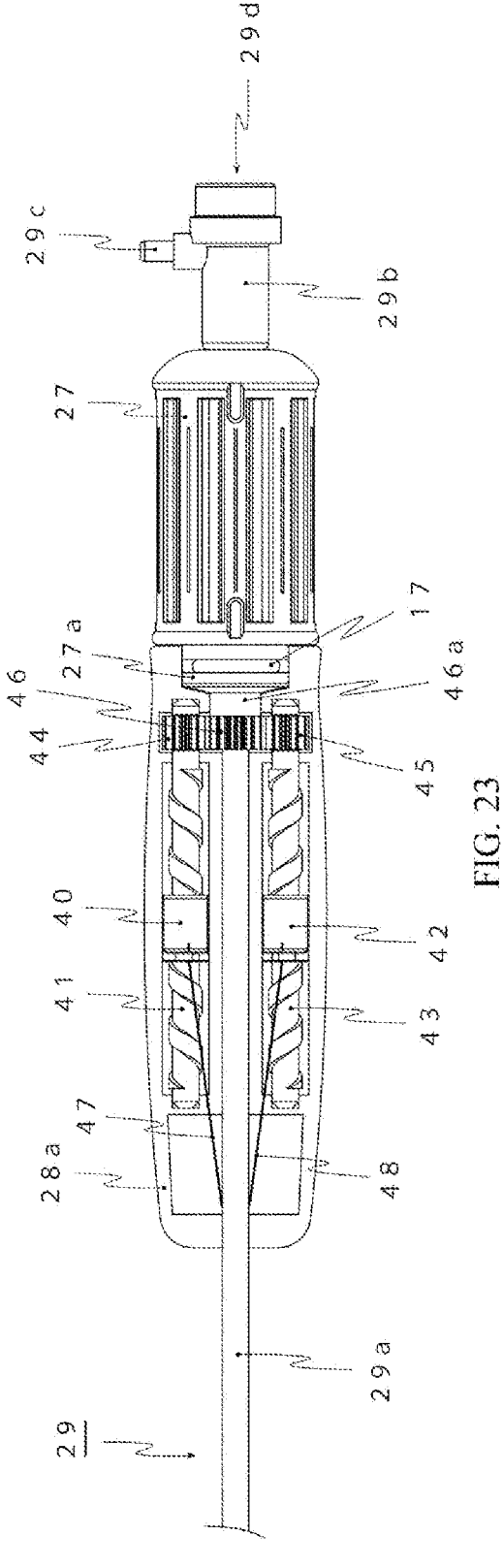
FIG. 23 is a plan view illustrating an internal mechanism of the medical device according to Embodiment 3 of the present disclosure. (The second case member is omitted.)

As shown in FIGS. 5 and 23, the first end of the first operation wire 47 is fixed at the head of the sheath tube 29*a*, and the second end of the first operation wire 47 is fixed at the first moving member 40. The first end of the second operation wire 48 is fixed at the head of the sheath tube 29*a*, and the second end of the second operation wire 48 is fixed at the second moving member 42. The first fixed part at which the first end of the first operation wire 47 is fixed and the second fixed part at which the first end of the second operation wire 48 is fixed are placed opposite to each other.

Figures 27A, 27B:
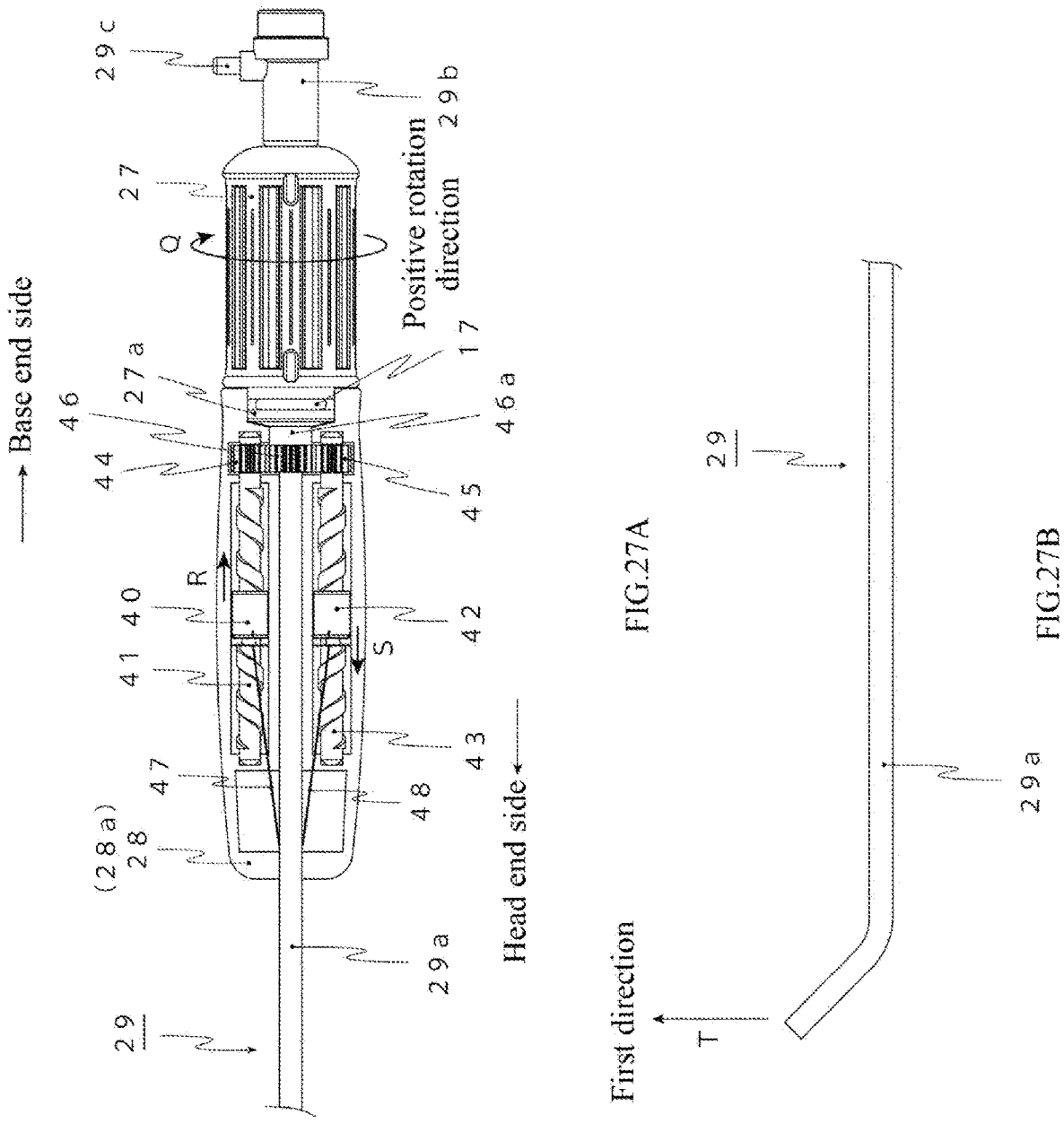
FIGS. 27A-27B are a plan view illustrating the first example use of the medical device according to Embodiment 3 of the present disclosure.

The first moving member 40 is moved to the base end side when the rotating operation part 27 is rotated in the positive rotation direction to allow the first operation wire 47 to deflect the head of the sheath tube 29*a* in a first direction (refer to FIGS. 27A-27B). The second moving member 42 is moved to the base end side when the rotating operation part 27 is rotated in the negative rotation direction opposite to the positive direction to allow the second operation wire 48 to deflect the head of the sheath tube 29*a* in a second direction opposite to the first rotation direction (refer to FIGS. 28A-28B). The number of the teeth of the first gear 44 and the number of the teeth of the second gear 45 are the same. The pitch of the male thread of the first feed rod 41 and the pitch of the male thread of the second feed rod 43 are also the same. Accordingly, the curve shape of the head of the sheath tube 29*a* when the rotating operation part 27 is rotated in the positive rotation direction is approximately the same as that when the rotating operation part 27 is rotated in the negative rotation direction. A preferred curving degree in the head of the sheath tube 29*a* can be maintained by stopping the rotation of the rotating operation part 27 at a preferred turning angle. Therefore, the curving shape of the head of the sheath tube 29*a* can be selected according to cases. The sheath tube 29*a* may uniformly flexible over throughout. However, a flexible part may be placed at the resin of the head end to make only the head end easy to curve.

The medical device 26 described above has the following function effect. Since the first moving member (first slide) 40 and the second moving member (second slide) 42 are placed away from each other, no transmission power is lost by friction generated between the two moving members (slides) 40 and 42. Therefore, since no strong torque transmitting to the rotating operation part (dial) 27 is necessary, the operability when the direction of the head of the sheath tube 29*a* is controlled can be improved.

As shown in FIGS. 21, 22 and 24 to 26, a ring-shaped concave groove 27*b* is formed at the head end 27*a* of the rotating operation part (dial) 27. An O-ring 17 as a friction member is put around the ring-shaped concave groove 27*b*. Thus, the O-ring 17 is placed around the outer edge of the main gear 46 of the rotating operation part 27. In the assembled medical device 26, the O-ring 17 is placed between the rotating operation part 27 and the handle case (gripper) 28, which produces frictional force between the rotating operation part 27 and the handle case (gripper) 28 when the rotating operation part 27 is operated to rotate.

The medical device 26 according to this Embodiment has the following function effect. The O-ring 17 is placed between the rotating operation part (dial) 27 and the handle case 28 as a friction member producing frictional force between the rotating operation part 27 and the handle case 28 when the rotating operation part 27 is operated to rotate. Accordingly, an appropriate load is applied to the operation of the handle 30 to rotate the rotating operation part 27 at an appropriate load not too heavily or lightly. Therefore, the medical device 26 according to this Embodiment can prevent the rotating operation part (dial) 27 from rotating more than the operator's intent and improve the operability to control the direction of the head of the sheath tube 29*a*.

According to the medical device 26 according to this Embodiment, the rotating operation part (dial) 27 can be prevented from inclining against the handle case 28 if the O-ring 17 as a friction member is provided between the rotating operation part (dial) 27 and the handle case 28. This always enables the rotating operation part (dial) 27 to be operated to smoothly rotate in the same way as the medical device 1 according to the above-mentioned Embodiment 1. Moreover, preventing the rotating operation part (dial) 27 from inclining against the handle case 28 contributes to improve "the pushability of the sheath tube 29*a*" that is described later.

In the medical device 26 according to this Embodiment, the O-ring 17 is placed between the rotating operation part (dial) 27 and the handle case 28 as a friction member producing frictional force between the rotating operation part 27 and the handle case 28 when the rotating operation part 27 is operated to rotate. Therefore, the rotating operation part (dial) 27 can be prevented from reversely rotating without the operator's intent in the same way as the above-mentioned Embodiment 1.

Figure 24:
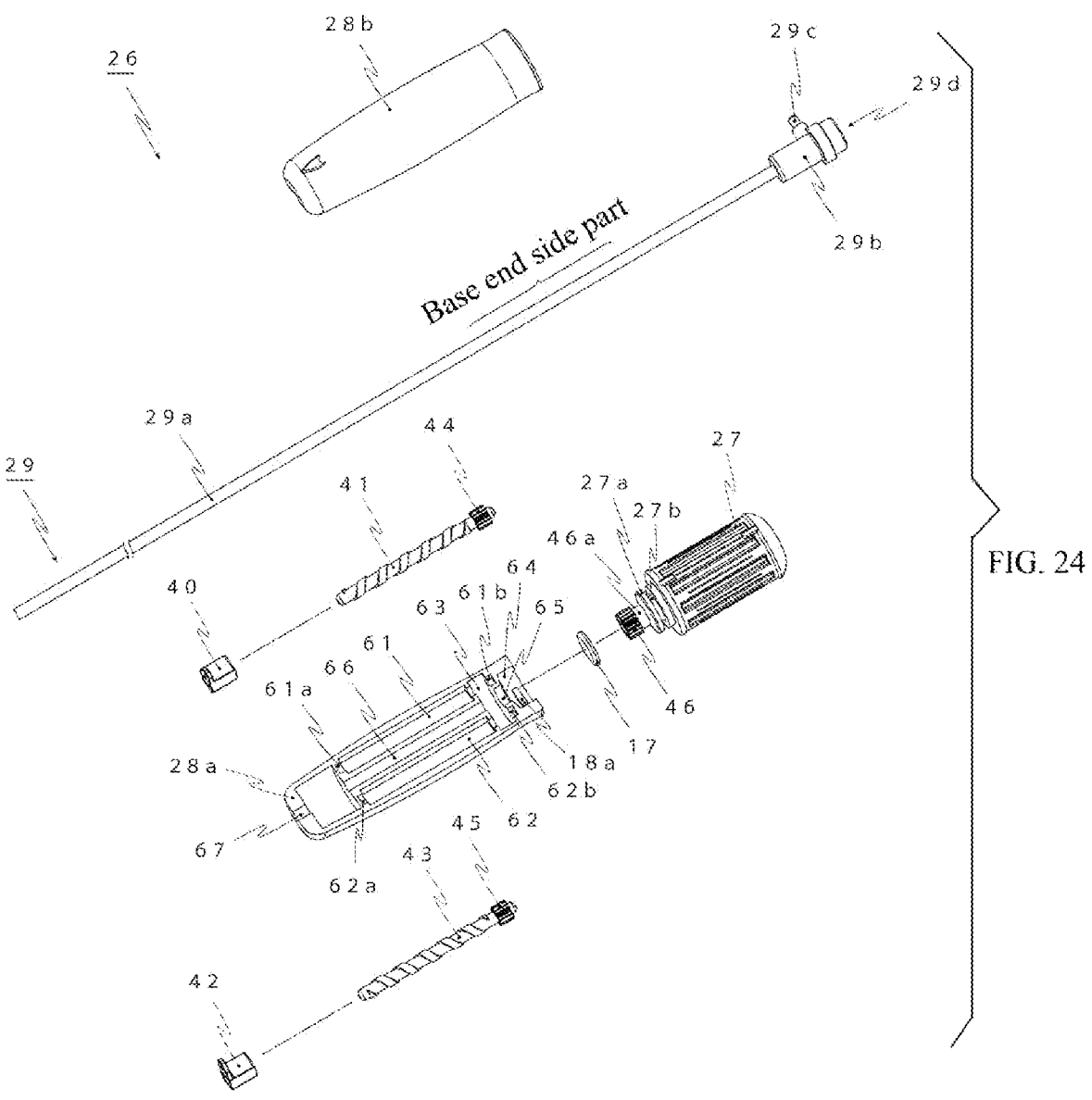
FIG. 24 is an exploded perspective view illustrating the components of the medical device according to Embodiment 3 of the present disclosure. (The first and the second operation wires are omitted.)
Figure 25:
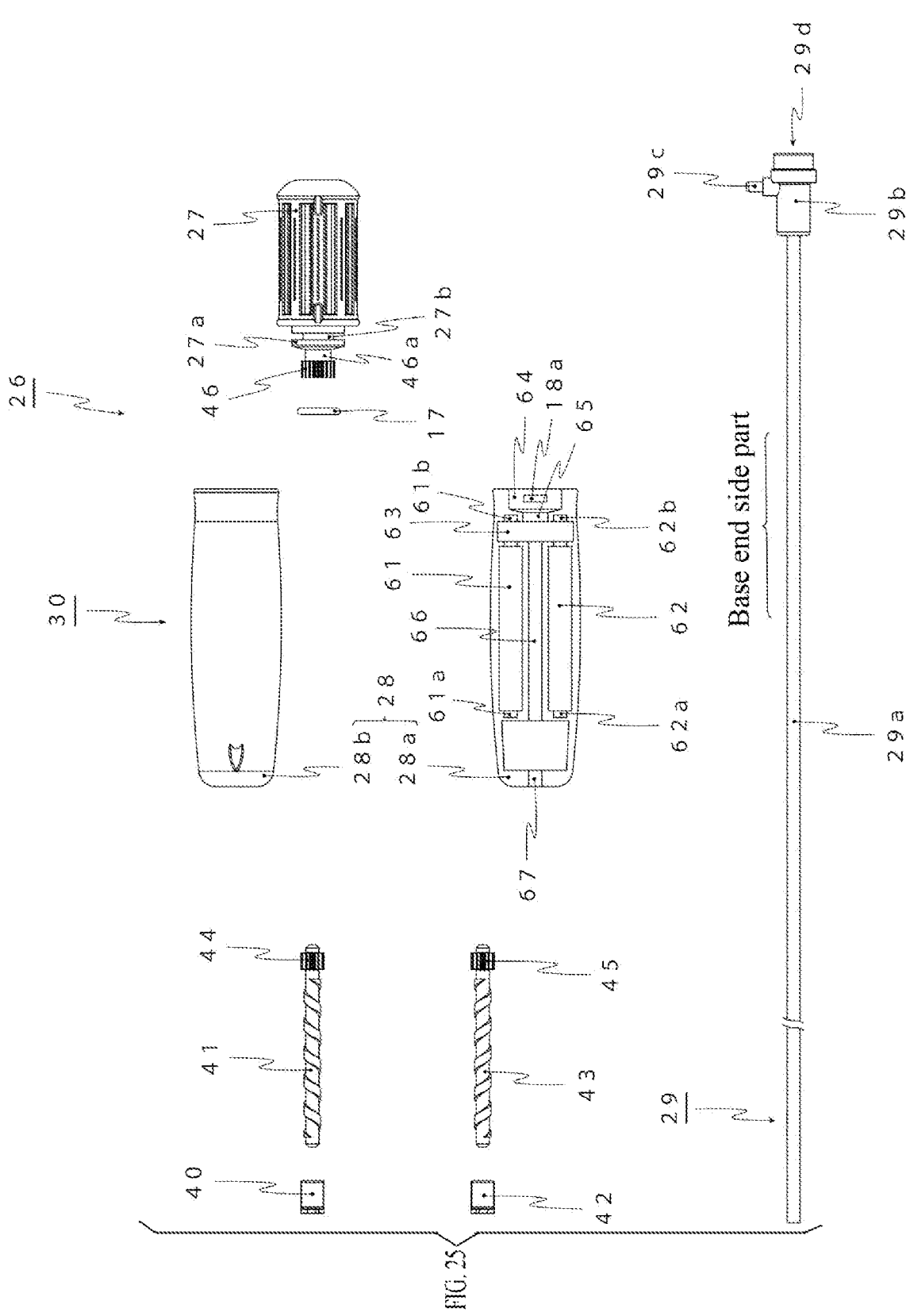
FIG. 25 is an exploded plan view illustrating the components of the medical device according to Embodiment 3 of the present disclosure. (The first and the second operation wires are omitted.)
Figure 26:
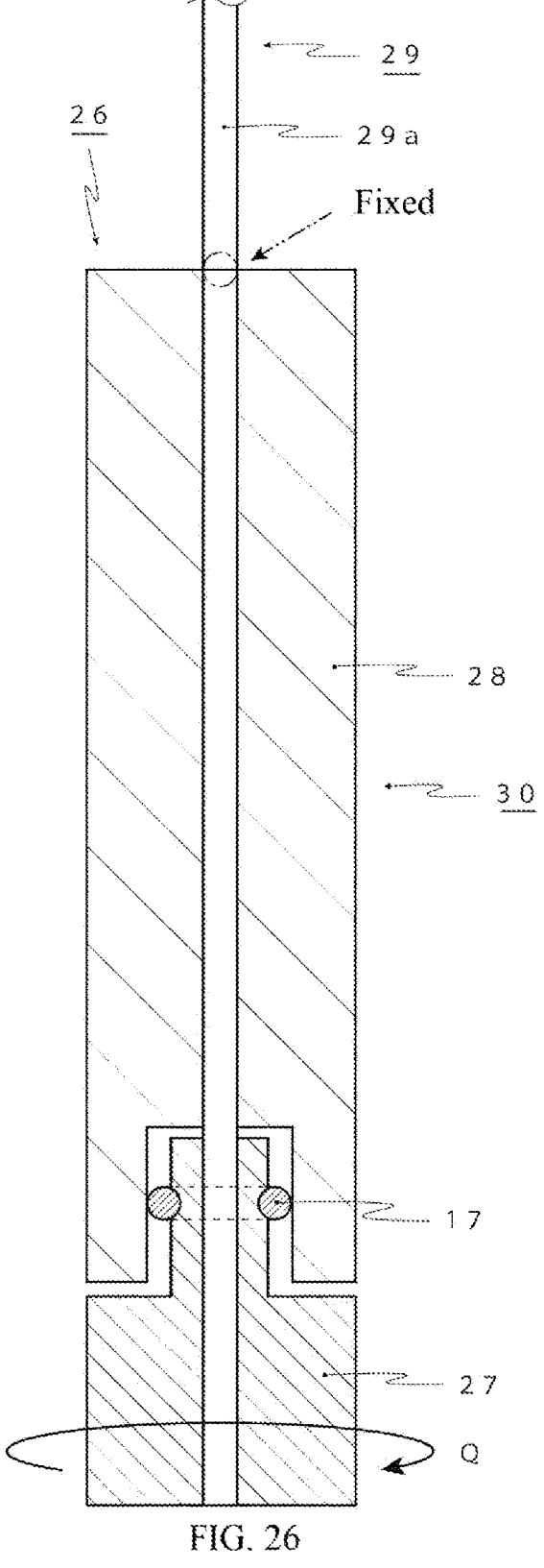
FIG. 26 is a pattern diagram illustrating the O-ring is put as a friction member of the medical device according to Embodiment 3 of the present disclosure.

The configuration of the medical device 26 of this Embodiment is more specifically described below. As shown in FIGS. 24 and 25, the first case member 28*a* and the second case member 28*b* that compose the handle case 28 are formed in an approximate semicircular column-shape. In the first case member 28*a* and the second case member 28*b*, multiple concaves and bearings are formed. The first case member 28*a* is explained below, but the second case member 28*b* is not because the second case member 28*b* has the same configuration as that of the first case member 28*a*.

In the first case member 28*a*, a first feed rod accommodating concave 61 and a second feed rod accommodating concave 62 that accommodates the first feed rod 41 and the second feed rod 43, respectively, are formed. The first feed rod accommodating concave 61 and the second feed rod accommodating concave 62 are formed in parallel at predetermined intervals along the longitudinal direction of the first case member 28*a*. The first feed rod accommodating concave 61 and the second feed rod accommodating concave 62 have the section crossing the longitudinal direction that is formed in an approximate rectangle-shape to enable the first moving member 40 and the second moving member 42, respectively, to move. In the head end side and the base end side of the first feed rod accommodating concave 61, bearings 61*a* and 61*b* that rotatably support the first feed rod 41 are formed. In the head end side and the base end side of the second feed rod accommodating concave 62, bearings 62*a* and 62*b* that rotatably support the second feed rod 43 are formed. In the back side of the first case member 28*a*, a gear accommodating concave 63 that accommodates the first gear 44, the second gear 45, and the main gear 46 engaging with the first gear 44 and the second gear 45 (refer to FIGS. 21 and 22) is formed. In the first case member 28*a*, a head end accommodating concave 64 that is located closer to the back side than the gear accommodating concave 63, which accommodates the head end 27*a* of the rotating operation part (dial) 27, and a bearing 65 that rotatably supports the gear axis 46*a* of the main gear 46 are formed. Moreover, in the first case member 28*a*, a sheath tube accommodating concave 66 that is located between the first feed rod accommodating concave 61 and the second feed rod accommodating concave 62, which accommodates the base end side part of the sheath tube 29*a*, is formed. At the base end of the first case member 28*a*, the second sheath tube accommodating concave 67 that accommodates the sheath tube 29*a* not rotatably (fixedly, refer to FIG. 26) is formed.

For the negative handle, the introducer sheath 29 is fixed at the head end side of the handle case 28 as described above so that the torque produced by the rotating operation of the handle case 28 can be easily transmitted to the sheath tube 29*a* (to enhance the torque transmissibility). Therefore, the sheath tube 29*a* is prevented from twisting by completely matching the rotation of the handle case 28 with that of the sheath tube 29*a* so that the rotation of the handle case 28 can be directly transmitted to the sheath tube 29*a*. Moreover, the pushability to certainly transmit pushing force from the operator to the head of the sheath tube 29*a* can be improved. Therefore, when the handle case 28 is pushed straight, the sheath tube 29*a* is also pushed straight.

As shown in FIGS. 20 to 22, 24 and 25, a through-hole (not shown) that passes through their common central axis is formed in the rotating operation part 27 and the gear axis 46*a* of the main gear 46. The sheath tube 29*a* can be passed through the through-hole.

As shown in FIGS. 5 and 23, in the sheath tube 29*a*, a first sublumen 29*f* and a second sublumen 29*g* are formed, extending from just front of the second sheath tube accommodating concave 67 (refer to FIGS. 24 and 25) to the head end in addition to a main lumen 29*e* that passes the dilator, etc. The first (head) ends of the first operation wire 47 and the second operation wire 48 that pass through the first sublumen 29*f* and the second sublumen 29*g*, respectively, are fixed to in the head end of the sheath tube 29*a* by a wire joint ring 15.

As shown in FIGS. 21, 22, 24, and 25, male threads are formed on the first feed rod 41 and the second feed rod 43, which are threaded reversely from each other. Moreover, female threads are formed on the first moving member 40 and the second moving member 42, which are threadably mounted on the first feed rod 41 and the second feed rod 43, respectively. Accordingly, the first feed rod 41 and the second feed rod 43 are rotated in the same direction to enable the first moving member 40 and the second moving member 42, respectively, to move in the directions opposite to each other on the first feed rod 41 and the second feed rod 43, respectively.

As shown in FIGS. 24 and 25, projections 18*a* and 18*b* (not shown) that are in contact with the O-ring 17 as a friction member are placed on the inner face of the handle case (gripper) 28. More specifically, the projection 18*a* is placed in the base end accommodating concave 64 of the first case member 28*a* that accommodates the head end 27*a* of the rotating operation part 27, and the projection 18*b* is placed in the head end accommodating concave 64 of the second case member 28*b*. Accordingly, the projections 18*a* and 18*b* are placed to face each other on the inner face of the handle case (gripper) 28. As shown in FIG. 20, in the assembled medical device 26, the O-ring 17 is in contact with the projections 18*a* and 18*b*, which produces frictional force between the O-ring 17 in the rotating operation part 27 side and the projections 18*a* and 18*b* in the handle case 28 side when the rotating operation part 27 is operated to rotate.

Accordingly, an appropriate load is applied to the rotating operation of the rotating operation part 27 to rotate the rotating operation part 27 at an appropriate load not too heavily or lightly. Therefore, the medical device 26 according to this Embodiment can prevent the rotating operation part 27 from rotating more than the operator's intent and improve the operability to control the direction of the head of the sheath tube 29*a*. Especially, a constant brake can be applied to the rotation of the rotating operation part 27 by adjusting the frictional force between the rotating operation part 27 and the handle case 28 by placing the projections 18*a* and 18*b* that are in contact with the O-ring 17 as a friction member on the inner face of the handle case 28. The above-mentioned variation of the number of the projections as shown in FIGS. 15A-15D enables the frictional force between the rotating operation part 27 and the handle case 28 to be adjusted.

The first case member 28*a* and the second case member 28*b* are set and detachably integrated with each other in set-in way in the same way as the first case member 12*a* and the second case member 12*b* according to the above-mentioned Embodiment 1.

Use of Medical Device

The use of the medical device according to Embodiment 3 of the present disclosure is described below with reference to FIGS. 27A-27B and 28A-28B.

The medical device 26 according to this Embodiment is used when a cardiac catheter is placed at an intended site in the same way as the medical device 1 according to the above-mentioned Embodiment 1. If necessary, the rotating operation part (dial) 27 is rotated to deflect the head of the sheath tube 29*a* and adjust the indwelling site of the cardiac catheter. For example, when the handle case 28 is gripped in one hand, and the rotating operation part 27 is rotated in a positive rotation direction in the other hand as shown in FIGS. 27A-27B (refer to the arrow Q of FIG. 27A), the first feed rod 41 and the second feed rod 43 rotate in the same direction (negative rotation direction) through the main gear 46, the first gear 44, and the second gear 45. Then, the first moving member 40 moves to the base end side (refer to the arrow R of FIG. 27A), and the second moving member 42 moves to the head side (refer to the arrow S of FIG. 27A). As the result, the first operation wire 47 is pulled to the base end side, the second operation wire 48 is loosened (refer to FIG. 5), and the head of the sheath tube 29*a* is deflected in the first direction toward the side (side port 29*c* side) from which the side tube comes out (refer to arrow T of FIG. 27B).

Figures 28A, 28B:
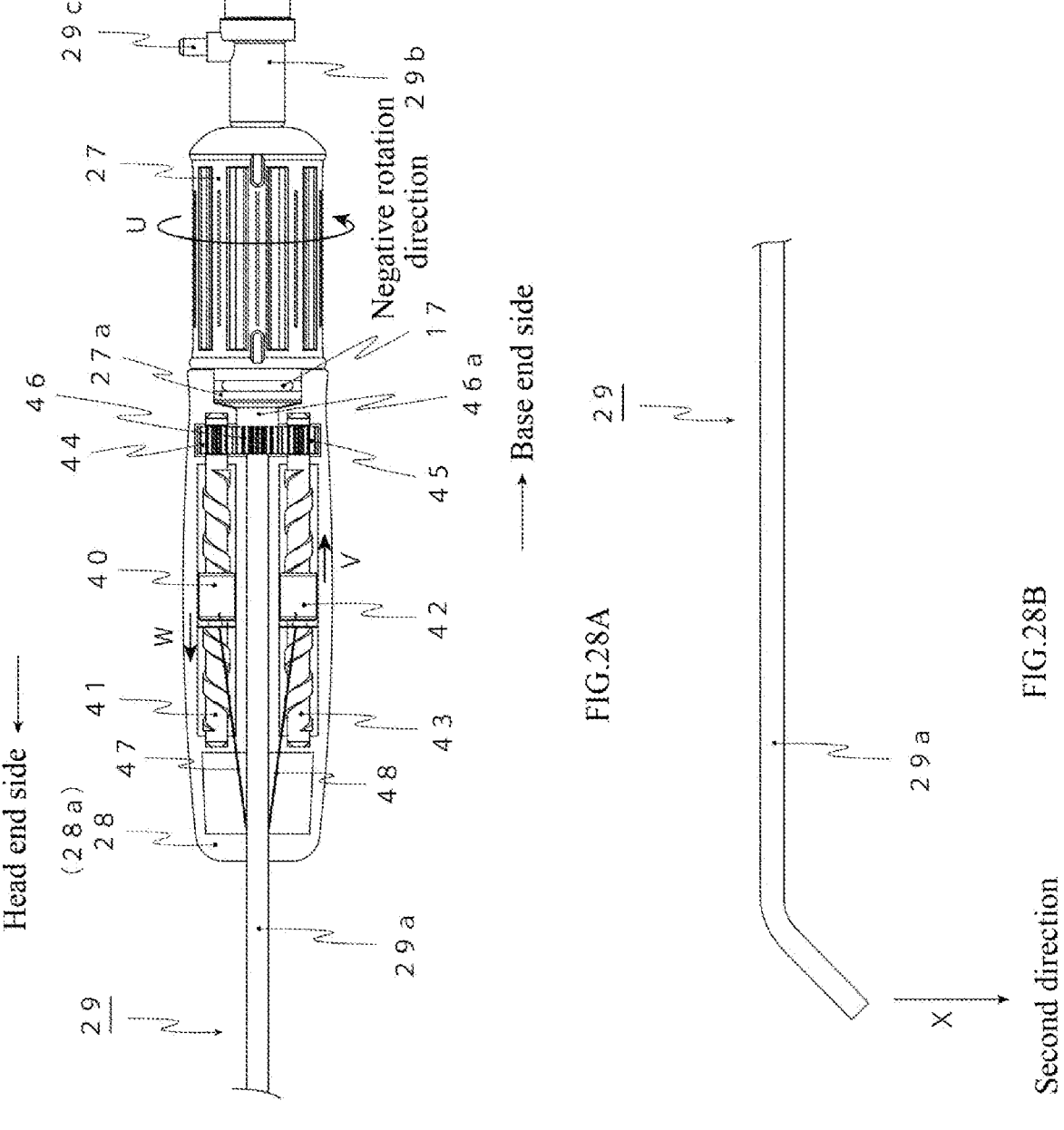
FIGS. 28A-28B are a plan view illustrating the second example use of the medical device according to Embodiment 3 of the present disclosure.

For example, when the handle case 28 is gripped in one hand, and the rotating operation part 27 is rotated in the negative rotation direction in the other hand as shown in FIGS. 28A-28B (refer to the arrow U of FIG. 28A), the first feed rod 41 and the second feed rod 43 rotate in the positive rotation direction through the main gear 46, the first gear 44, and the second gear 45. Then, the second moving member 42 moves to the base end side (refer to the arrow V of FIG. 28A), and the first moving member 40 moves to the head side (refer to the arrow W of FIG. 28A). As the result, the second operation wire 48 is pulled to the base end side, the first operation wire 47 is loosened (refer to FIG. 5), and the head of the sheath tube 29*a* is deflected in the second direction opposite to the side (side port 29*c* side) from which the side tube comes out (refer to arrow X of FIG. 28B).

Accordingly, since the indwelling site of the cardiac catheter can be adjusted, the cardiac catheter can be placed at an intended site correctly. The deflecting direction has been explained, giving an example of the side (side port 29*c* side) from which the side tube comes out. However, the deflecting direction of the present disclosure is not limited to the basis of such an example. The head of the sheath tube 29*a* only has to deflect in the opposite direction.

This Embodiment has been explained, giving an example where the introducer sheath 29 is used for inserting a cardiac catheter from a blood vessel into the atrium and ventricles as the tubular member. However, the present disclosure is not necessarily limited to such an example. The tubular member may be another tubular member for a catheter, an endoscope, etc., as long as it has flexibility.

This Embodiment has been explained, giving an example where the curve shape of the head of the sheath tube 29*a* when the rotating operation part 27 is rotated in the positive rotation direction is approximately the same as that when the rotating operation part 27 is rotated in the negative rotation direction. However, the present disclosure is not necessarily limited to such an example. The curve shape of the head of the sheath tube 29*a* when the rotating operation part 27 is rotated in the positive rotation direction may be different from that when the rotating operation part 27 is rotated in the negative rotation direction. Accordingly, the two different shapes of curve can be used by one sheath tube 29*a* to enable the head to reach a number of sites. In this case, the tension resistance of the first operation wire 47 may be different from that of the second operation wire 48. However, the easiness of the rotation in the positive or negative rotation direction of the rotating operation part (dial) 27 can be controlled by changing of the numbers of the teeth of the first gear 44 and the second gear 45 or the pitches of the male threads of the first feed rod 41 and the second feed rod 43.

Furthermore, this Embodiment has been explained, giving an example where the O-ring 17 is used as a friction member. However, the present disclosure is not necessarily limited to such an example. As a friction member other than the O-ring, for example, a C-ring, an O-ring with bumps and dips in its circumference, gel, fluid, and particles can be used.

In this Embodiment, an indicator may be provided near the rotating operation part (dial) 27 in the same way as the medical device 60 according to the above-mentioned Embodiment 2.

DESCRIPTION OF REFERENCE NUMERALS

1, 23, 26, 50, 54, 60: medical device, 2, 40: first moving member, 3, 41: first feed rod, 4, 42: second moving member, 5, 43: second feed rod, 6, 47: first operation wire, 7, 48: second operation wire, 8, 44: first gear, 9, 45: second gear, 10, 46: main gear, 10*a*, 46*a*: gear axis, 11, 24, 27, 51, 55: rotating operation part (dial), 11*a*: base end, 11*b*, 24*a*, 27*b*, 51*a*: concave groove, 12, 28: handle case (gripper), 12*a*, 28*a*: first case member (first gripper member), 12*b*, 28*b*: second case member (second gripper member), 13, 29: introducer sheath, 13*a*, 29*a*: sheath tube, 13*b*, 29*b*: sheath hub, 13*c*, 29*c*: side port, 13*d*, 29*d*: dilator insertion opening, 13*e*, 29*e*: main lumen, 13*f*, 29*f*: first sublumen, 13*g*, 29*g*: second sublumen, 14, 30: handle, 15: wire joint ring, 17, 25, 57: O-ring (friction member), 18*a*, 18*b*, 18*c*, 18*c*1, 18*c*2, 18*d*, 18*d*1, 18*d*2, 18*e*, 18*e*1, 18*e*2: projection, 19: first tab, 20: second tab, 21: scale, 27*a*: head end, 31, 61: first feed rod accommodating concave, 31*a*, 31*b*, 32*a*, 32*b*, 35, 61*a*, 61*b*, 62*a*, 62*b*, 65: bearing, 32, 62: second feed rod accommodating concave, 33, 63: gear accommodating concave, 34: base end accommodating concave, 36, 66: sheath tube accommodating concave, 37, 64: head end accommodating concave, 56: window, 67: second sheath tube accommodating concave

The invention claimed is:

1. A medical device comprising:
a flexible tubular member;
a rotating operation part that deflects a head of the tubular member in a first direction when rotating in positive rotation direction and deflects the head of the tubular member in a second direction when rotating in negative rotation direction opposite to the positive direction;
a gripper that is gripped when the rotating operation part is rotated; and
an O-ring mounted between the rotating operation part and the gripper produces frictional force in the direction opposite to the rotation direction of the rotating operation part between the rotating operation part and the gripper when the rotating operation part is operated to rotate, wherein at least two projections placed on an inner face of the gripper are in contact with the O-ring and adjust the frictional force in a direction opposite to a rotation direction of the rotating operation part.

2. The medical device according to claim 1, further comprising a second friction member mounted between the rotating operation part and the tubular member and produces frictional force in the direction opposite to the rotation direction of the rotating operation part between the rotating operation part and the tubular member when the rotating operation part is operated to rotate.

3. The medical device according to claim 1, further comprising:

a first feed rod where a first moving member moves;

a second feed rod where a second moving member moves;

a first operation wire having a first end fixed to the head of the tube member and a second end fixed to one of the first moving member or a first other member working with the first moving member;

a second operation wire having a first end fixed to the head of the tube member and a second end fixed to one of the second moving member or a second other member working with the second moving member;

a first gear fixed to the first feed rod;

a second gear fixed to the second feed rod; and a main gear placed between the first gear and the second gear and rotates by rotating the rotating operation part to transmit rotary driving force to the first gear and the second gear, wherein the first moving member is moved to a base end side when the rotating operation part is rotated in the positive rotation direction to allow the first operation wire to deflect the head of the tubular member in the first direction, and the second moving member is moved to the base end side when the rotating operation part is rotated in the negative rotation direction to allow the second operation wire to deflect the head of the tubular member in the second direction.

4. The medical device according to claim 3, wherein first moving member moves on the first feed rod in a longitudinal direction, and the second moving member moves on the second feed rod in a longitudinal direction.

5. The medical device according to claim 3, wherein the main gear transmits rotary driving force in a same direction as those of the first gear and the second gear.

6. The medical device according to claim 1, wherein the rotating operation part is located in a head side of the gripper.

7. The medical device according to claim 6, wherein the tubular member is fixed in a base end side of the gripper.

8. The medical device according to claim 6, wherein the first gear is fixed at a head end of the first feed rod, and the second gear is fixed at a head end of the second feed rod.

9. The medical device according to claim 1, wherein the rotating operation part is located in a base side of the gripper.

10. The medical device according to claim 9, wherein the head of the tubular member is fixed in a head end side of the gripper.

11. The medical device according to claim 9, wherein the first gear is fixed at a back end of the first feed rod, and the second gear is fixed at a back end of the second feed rod.

12. The medical device according to claim 1, wherein the gripper includes a first gripper member and a second gripper member that are approximately semicircular column-shaped and mounted opposite to each other, and the first gripper member and the second gripper member are detachably integrated with each other.

13. The medical device according to claim 1, further comprising a display provided in a part of the rotating operation part that is inserted into the gripper, the display indicating a turning angle of the head of the tubular member along a circumferential direction, and a window in the gripper through which the display can be viewed from outside.

14. The medical device according to claim 1, wherein two projections are in contact with the O-ring and are placed to face each other on the inner face of the gripper.

15. The medical device according to claim 1, wherein four projections are placed on the inner face of the gripper to make contact with the O-ring in a circumferential direction at intervals of approximately 90 degrees.

* * * * *